US012744121B2

(12) United States Patent
Couture et al.

(10) Patent No.: US 12,744,121 B2
(45) Date of Patent: Sep. 22, 2026

(54) ROBOTICALLY-ASSISTED SURGICAL PROCEDURE FEEDBACK TECHNIQUES

(71) Applicant: MedTech S.A., Montpellier (FR)

(72) Inventors: Pierre Couture, Montreal (CA); William Hartman, Warsaw, IN (US)

(73) Assignee: MedTech S.A., Montpellier (FR)

( * ) Notice: Subject to any disclaimer, the term of this patent is extended or adjusted under 35 U.S.C. 154(b) by 26 days.

(21) Appl. No.: 18/606,557

(22) Filed: Mar. 15, 2024

(65) Prior Publication Data

US 2024/0371509 A1 Nov. 7, 2024

Related U.S. Application Data

(63) Continuation of application No. 16/284,622, filed on Feb. 25, 2019, now Pat. No. 11,967,422.
(Continued)

(51) Int. Cl.
*G16H 40/63* (2018.01)
*A61B 5/00* (2006.01)
(Continued)

(52) U.S. Cl.
CPC ............ *G16H 40/63* (2018.01); *A61B 5/117* (2013.01); *A61B 5/7267* (2013.01); *A61B 5/746* (2013.01); *A61B 34/10* (2016.02); *A61B 34/32* (2016.02); *A61F 2/461* (2013.01); *G06F 16/2455* (2019.01); *G06N 20/00* (2019.01);
(Continued)

(58) Field of Classification Search
USPC .......................................................... 705/2-3
See application file for complete search history.

(56) References Cited

U.S. PATENT DOCUMENTS 5,499,293 A 3/1996 Behram et al.
8,498,883 B2 7/2013 Lorsch
(Continued)

FOREIGN PATENT DOCUMENTS

CA 2980618 A1 9/2016
EP 2380626 A1 10/2011
(Continued)

OTHER PUBLICATIONS

Wang, Z., Majewicz Fey, A. Deep learning with convolutional neural network for objective skill evaluation in robot-assisted surgery. Int J CARS 13, 1959-1970 (2018). https://doi.org/10.1007/s11548-018-1860-1 (Year: 2018).*
(Continued)

*Primary Examiner* — Bennett Stephen Erickson
(74) *Attorney, Agent, or Firm* — SCHWEGMAN LUNDBERG & WOESSNER, P.A.

(57) ABSTRACT

A system and method for pre-operative or intra-operative surgical procedure feedback provide a recommendation to a surgeon. A system may include a robotic surgical device to perform a portion of a surgical procedure on a patient, and a processor to determine a recommendation, based on past surgical information, for the portion of the surgical procedure performed by the robotic surgical device or for a next action to be taken, but the robotic surgical device or a surgeon. The system may include outputting the recommendation by intra-operatively providing the recommendation to a surgeon operating the robotic surgical device.

20 Claims, 13 Drawing Sheets

Related U.S. Application Data

(60) Provisional application No. 62/638,492, filed on Mar. 5, 2018.

(51) Int. Cl.

| | |
|---|---|
| ***A61B 5/117*** | (2016.01) |
| ***A61B 34/10*** | (2016.01) |
| ***A61B 34/32*** | (2016.01) |
| ***A61F 2/46*** | (2006.01) |
| ***G06F 16/2455*** | (2019.01) |
| ***G06N 20/00*** | (2019.01) |

(52) U.S. Cl.
CPC ... *A61B 2034/104* (2016.02); *A61B 2034/105* (2016.02); *A61F 2002/4632* (2013.01)

(56) References Cited

U.S. PATENT DOCUMENTS

| | | | | |
|---|---|---|---|---|
| 9,700,292 | B2 | 7/2017 | Nawana et al. | |
| 9,788,907 | B1 | 10/2017 | Alvi et al. | |
| 10,216,904 | B2 | 2/2019 | Hughes et al. | |
| 10,226,302 | B2 | 3/2019 | Lacal et al. | |
| 10,568,535 | B2 * | 2/2020 | Roberts | A61B 5/0042 |
| 11,158,415 | B2 | 10/2021 | Daley et al. | |
| 11,967,422 | B2 | 4/2024 | Couture et al. | |
| 2011/0020779 | A1 | 1/2011 | Hannaford et al. | |
| 2014/0046128 | A1 * | 2/2014 | Lee | A61B 34/37 600/102 |
| 2014/0052999 | A1 * | 2/2014 | Aissi | G06F 21/64 713/189 |
| 2016/0210442 | A1 | 7/2016 | Ethington et al. | |
| 2016/0314711 | A1 | 10/2016 | Grubbs | |
| 2017/0228517 | A1 | 8/2017 | Saliman et al. | |
| 2017/0372029 | A1 | 12/2017 | Saliman et al. | |
| 2018/0055577 | A1 | 3/2018 | Barral et al. | |
| 2018/0233222 | A1 | 8/2018 | Daley et al. | |
| 2018/0263535 | A1 | 9/2018 | Cramer | |
| 2019/0008598 | A1 | 1/2019 | Frimer et al. | |
| 2019/0065970 | A1 | 2/2019 | Bonutti et al. | |
| 2019/0206563 | A1 * | 7/2019 | Shelton, IV | G16H 50/20 |
| 2019/0206565 | A1 | 7/2019 | Shelton, IV | |
| 2019/0272917 | A1 | 9/2019 | Couture et al. | |
| 2020/0000400 | A1 | 1/2020 | Mckinnon et al. | |
| 2021/0065870 | A1 | 3/2021 | Spooner et al. | |
| 2021/0233615 | A1 | 7/2021 | Banavar et al. | |

FOREIGN PATENT DOCUMENTS

| | | | |
|---|---|---|---|
| EP | 3790019 | A1 | 3/2021 |
| EP | 3790019 | B1 | 8/2024 |
| GB | 2505067 | B | 3/2015 |
| WO | WO-2017083768 | A1 | 5/2017 |
| WO | WO-2017214656 | A1 | 12/2017 |

OTHER PUBLICATIONS

"U.S. Appl. No. 16/560,793, Reply Brief mailed May 6, 2024", 13 pgs.
"Australian Application Serial No. 2022203648, Response filed May 13, 2024 to First Examination Report mailed Jun. 9, 2023", 32 pgs.
"Australian Application Serial No. 2022203648, Subsequent Examination Report mailed May 29, 2024", 6 pgs.
"European Application Serial No. 21179139.7, Communication Pursuant to Article 94(3) EPC mailed Mar. 15, 2024", 9 pgs.
"European Application Serial No. 21179139.7, Response filed Jul. 15, 2024 to Communication Pursuant to Article 94(3) EPC mailed Mar. 15, 2024", 15 pgs.
Patel, Shyamal, et al., "A review of wearable sensors and systems with application in rehabilitation", Journal of NeuroEngineering and Rehabilitation 9(21), (2012), 17 pgs.
"U.S. Appl. No. 16/560,793, Appeal Decision mailed May 16, 2025", 21 pgs.
"U.S. Appl. No. 16/560,793, Final Office Action mailed Aug. 21, 2025", 12 pgs.
"U.S. Appl. No. 16/284,622, Advisory Action mailed Jun. 14, 2021", 3 pgs.
"U.S. Appl. No. 16/284,622, Appeal Brief filed Dec. 22, 2022", 21 pgs.
"U.S. Appl. No. 16/284,622, Appeal Decision mailed Sep. 28, 2023", 11 pgs.
"U.S. Appl. No. 16/284,622, Examiner Interview Summary mailed May 24, 2022", 2 pgs.
"U.S. Appl. No. 16/284,622, Examiner's Answer mailed Mar. 14, 2023", 16 pgs.
"U.S. Appl. No. 16/284,622, Final Office Action mailed Mar. 23, 2021", 25 pgs.
"U.S. Appl. No. 16/284,622, Final Office Action mailed Apr. 13, 2022", 26 pgs.
"U.S. Appl. No. 16/284,622, Non Final Office Action mailed Aug. 13, 2020", 26 pgs.
"U.S. Appl. No. 16/284,622, Non Final Office Action mailed Aug. 19, 2022", 24 pgs.
"U.S. Appl. No. 16/284,622, Non Final Office Action mailed Oct. 26, 2021", 31 pgs.
"U.S. Appl. No. 16/284,622, Notice of Allowability mailed Jan. 8, 2024", 3 pgs.
"U.S. Appl. No. 16/284,622, Notice of Allowance mailed Dec. 14, 2023", 21 pgs.
"U.S. Appl. No. 16/284,622, Reply Brief filed May 12, 2023", 10 pgs.
"U.S. Appl. No. 16/284,622, Response filed Jan. 13, 2021 to Non Final Office Action mailed Aug. 13, 2020", 11 pgs.
"U.S. Appl. No. 16/284,622, Response filed Jan. 26, 2022 to Non Final Office Action mailed Oct. 26, 2021", 14 pgs.
"U.S. Appl. No. 16/284,622, Response filed May 24, 2021 to Final Office Action mailed Mar. 23, 2021", 12 pgs.
"U.S. Appl. No. 16/284,622, Response filed Jun. 23, 2021 to Advisory Action mailed Jun. 14, 2021", 16 pgs.
"U.S. Appl. No. 16/284,622, Response filed Jul. 13, 2022 to Final Office Action mailed Apr. 13, 2022", 13 pgs.
"U.S. Appl. No. 16/560,793, Appeal Brief filed Nov. 14, 2023", 22 pgs.
"U.S. Appl. No. 16/560,793, Examiner Interview Summary mailed Jan. 13, 2023", 2 pgs.
"U.S. Appl. No. 16/560,793, Examiner Interview Summary mailed May 8, 2023", 2 pgs.
"U.S. Appl. No. 16/560,793, Examiner Interview Summary mailed Jul. 11, 2022", 2 pgs.
"U.S. Appl. No. 16/560,793, Examiner Interview Summary mailed Aug. 27, 2021", 2 pgs.
"U.S. Appl. No. 16/560,793, Final Office Action mailed Jan. 6, 2022", 18 pgs.
"U.S. Appl. No. 16/560,793, Final Office Action mailed Feb. 17, 2023", 20 pgs.
"U.S. Appl. No. 16/560,793, Final Office Action mailed Nov. 25, 2022", 21 pgs.
"U.S. Appl. No. 16/560,793, Non Final Office Action mailed May 25, 2022", 19 pgs.
"U.S. Appl. No. 16/560,793, Non Final Office Action mailed Jun. 14, 2023", 19 pgs.
"U.S. Appl. No. 16/560,793, Non Final Office Action mailed Jun. 24, 2021", 16 pgs.
"U.S. Appl. No. 16/560,793, Response filed Apr. 6, 2022 to Final Office Action mailed Jan. 6, 2022", 14 pgs.
"U.S. Appl. No. 16/560,793, Response filed May 17, 2023 to Final Office Action mailed Feb. 17, 2023", 19 pgs.
"U.S. Appl. No. 16/560,793, Response filed Aug. 25, 2022 to Non Final Office Action mailed May 25, 2022", 15 pgs.
"U.S. Appl. No. 16/560,793, Response filed Sep. 24, 2021 to Non Final Office Action mailed Jun. 24, 2021", 16 pgs.
"Australian Application Serial No. 2020227004, First Examination Report mailed May 31, 2021", 5 pgs.

(56) References Cited

OTHER PUBLICATIONS

"Australian Application Serial No. 2020227004, Response filed 01-21-022 to First Examination Report mailed May 31, 2021", 49 pgs.
"Australian Application Serial No. 2020227004, Response filed Mar. 25, 2022 to Subsequent Examiners Report mailed Feb. 15, 2022", 24 pgs.
"Australian Application Serial No. 2020227004, Subsequent Examiners Report mailed Feb. 15, 2022", 5 pgs.
"Australian Application Serial No. 2020227004, Subsequent Examiners Report mailed Apr. 20, 2022", 4 pgs.
"Australian Application Serial No. 2022203648, First Examination Report mailed Jun. 9, 2023", 3 pgs.
"European Application Serial No. 19160858.7, Communication Pursuant to Article 94(3) EPC mailed Apr. 1, 2020", 8 pgs.
"European Application Serial No. 19160858.7, Extended European Search Report mailed Jul. 18, 2019", 8 pgs.
"European Application Serial No. 19160858.7, Response filed Mar. 11, 2020 to Extended European Search Report mailed Jul. 18, 2019", 17 pgs.
"European Application Serial No. 19160858.7, Summons to Attend Oral Proceedings mailed Sep. 14, 2020", 12 pgs.
"European Application Serial No. 20194416.2, Extended European Search Report mailed Jan. 28, 2021", 13 pgs.
"European Application Serial No. 20194416.2, Response filed Sep. 10, 2021 to Extended European Search Report mailed Jan. 28, 2021", 29 pgs.
"European Application Serial No. 21179139.7, Response filed Jul. 12, 2022 to Extended 'European Search Report mailed Dec. 14, 2021", 30 pgs.
"European Application Serial No. 21179139.7, Extended European Search Report mailed Dec. 14, 2021", 10 pgs.
Hossain, Belayat, et al., "Implanted Knee Kinematics Prediction: comparative performance analysis of machine learning techniques", Joint 7th International Conference on Informatics, Electronics & Vision (ICIEV) and 2018 2nd International Conference on G16H50/70 Imaging, Vision & Pattern Recognition (ICIVPR), IEEE, (Jun. 25, 2018), 544-549.
Prem, Ramkumar N, et al., "Remote Patient Monitoring Using Mobile Health for Total Knee Arthroplasty: Validation of a Wearable and Machine Learning-Based Surveillance Platform", The Journal of Arthroplasty, Churchill Livingstone, Amsterdam, NL, vol. 34, No. 10, (May 16, 2019), 2253-2259.
Tan, Tina, "How Verb Surgical Will Deliver on Surgery 4.0", Clinica; https://medtech.pharmaintelligence.informa.com/MT121764/Exec-Chat-How-Verb-Surgical-Will-Deliver-On-Surgery-40, (Nov. 14, 2017), 5 pgs.
"U.S. Appl. No. 16/560,793, Examiner's Answer to Appeal Brief mailed Mar. 6, 2024", 11 pgs.
"U.S. Appl. No. 16/560,793, Examiner Interview Summary mailed Sep. 25, 2025", 2 pgs.
"U.S. Appl. No. 16/560,793, Response filed Oct. 20, 2025 to Final Office Action mailed Aug. 21, 2025", 19 pgs.
"U.S. Appl. No. 16/560,793, Advisory Action mailed Oct. 24, 2025", 3 pgs.
"U.S. Appl. No. 16/560,793, Non Final Office Action mailed Dec. 1, 2025", 13 pgs.
Momi, E. De, "ROBOt and sensors integration for computer assisted surgery and therapy (ICT-2007-215190-Robocast)", 2009 International Conference on Advanced Robotics, Munich, Germany, (2009), 1-6.

* cited by examiner

802

INITIAL SURGICAL PLAN

PLAN LOADED

804

POST OP RECORD TRANSFERRED TO THUMB DRIVE

806

DATA LOADED TO LAPTOP

808

LAPTOP CONNECTS VIA SECURE INTERNET LINK

INTERNET

810

DATA TRANSFERRED TO SECURE SERVER

812

ROBOTICALLY-ASSISTED SURGICAL PROCEDURE FEEDBACK TECHNIQUES

CLAIM OF PRIORITY

This application is a continuation of U.S. patent application Ser. No. 16/284,622, filed on Feb. 25, 2019, which claims the benefit of U.S. Provisional Patent Application Ser. No. 62/638,492, filed on Mar. 5, 2018, the benefit of priority of which is claimed hereby, and which is incorporated by reference herein in its entirety.

BACKGROUND

Diagnostics are used to evaluate a patient to determine whether the patient needs a surgical procedure, such as a total hip arthroplasty, ligament repair, knee replacement, shoulder replacement, or the like. These procedures are performed hundreds of thousands of times a year in the United States. Surgical advancements have allowed surgeons to use preoperative planning, display devices, and imaging, to improve diagnoses and surgical outcomes. Computer-assisted surgery is a growing field that encompasses a wide range of devices, uses, procedures, and computing techniques, such as surgical navigation, pre-operative planning, and various robotic techniques. However, when performing these techniques, patient outcomes are difficult to determine, and sometimes remain unknown.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
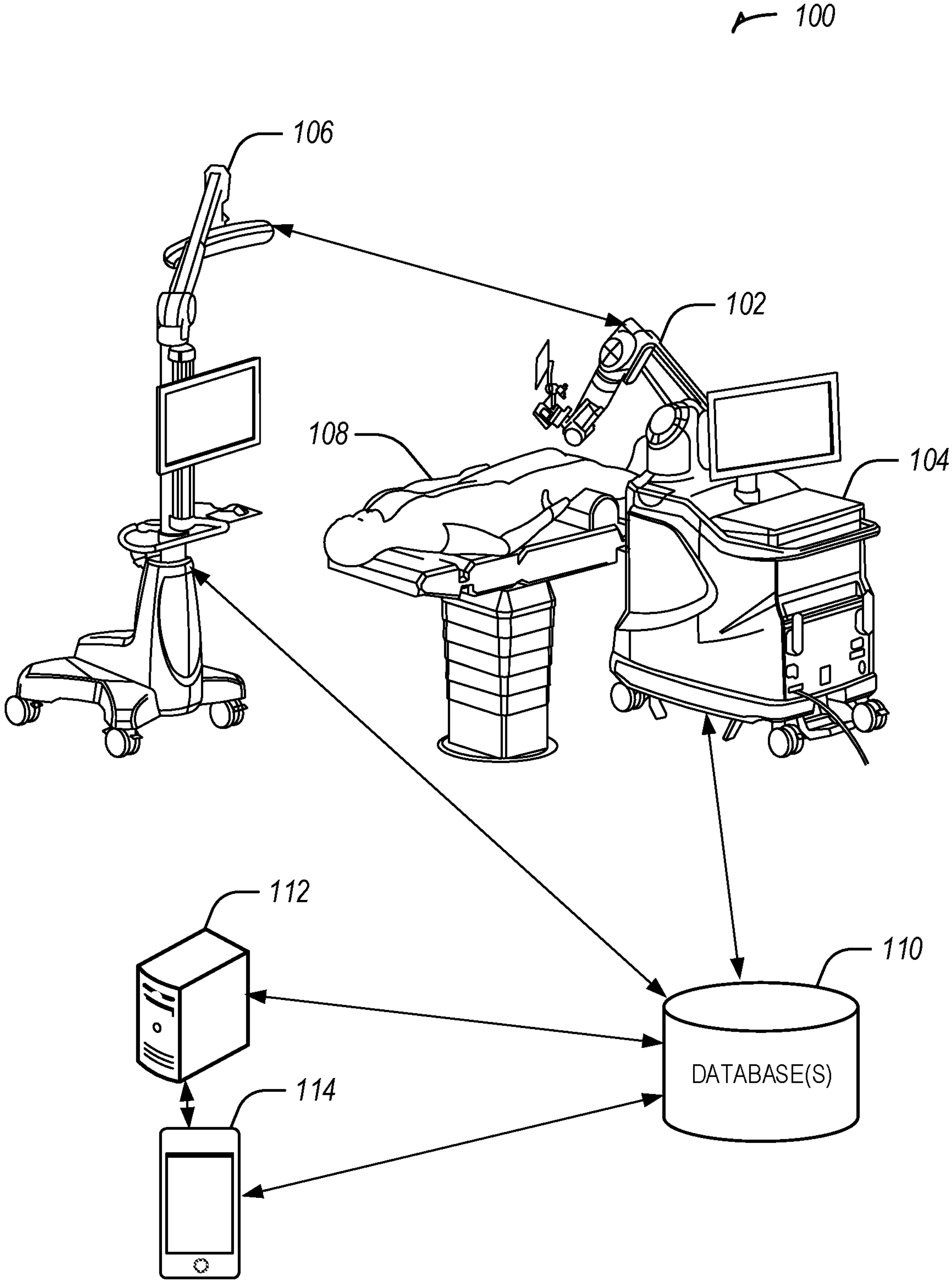
FIG. 1 illustrates a robotic surgery and feedback system in accordance with some embodiments.

Systems and methods for determining and providing a recommendation or an alert for a change in a surgical procedure based on data collected and analyzed from a portion of a previous surgical procedure performed or recorded using a robotic surgical device are described herein. The systems and methods herein may include a robotic surgical device to perform or record an operation or information about a surgical procedure. For example, the robotic surgical device may be used to perform a portion of a surgical procedure, such as a soft tissue balancing test in a knee arthroplasty, and record specific detailed information about the surgical procedure. The information recorded may include parameters of operations performed by the robotic surgical device, patient information, details about the procedure, metadata (e.g., date, time, temperature, pressure, etc.), or the like. For example, in a robotically assisted knee arthroplasty, the robot may assist in operations such as soft tissue balancing and bone resections. Specific objective parameters from these operations may be recorded in association with this patient (e.g., soft tissue tension numbers for medial and lateral sides of the knee and resection angles). Recording of these types of specific information may then be correlated with the specific patient's outcome at a later date when the success of the overall procedure can be fully evaluated. Recording and correlation of pre-operative, intra-operative, and post-operative information may then be utilized in real-time to provide evidence based recommendations for procedures encountering similar surgical situations.

The systems and methods described herein may be used to provide a recommendation to a surgeon based on a surgical plan, intraoperatively in response to a request, or as an alert when a critical issue or recommendation event is identified. The recommendation or alert may be determined based on past recorded information, patient provided outcomes, sensor data (e.g., from a sensor coupled to an implant), metadata, a model trained in a machine learning system, or the like. Information collected during a surgical procedure may be automatically stored at the robotic surgical device. The stored information may be transmitted or transferred to a secure server or database for later use. In an example, the information may be anonymized, such as until a user (e.g., a patient) opts in to using the data. In an example, the information may be stored in a manner that makes the data inaccessible or encrypted (e.g., until the patient opts in). In certain examples, the data is never directly associated with a specific patient, but rather the pre-operative, intra-operative, and post-operative information is anonymously correlated to create patterns of pre-operative deformities correlated with successful intra-operative interventions.

The systems and methods described herein may use received patient opt in, such as by receiving submission of patient outcome information (e.g., pain details, an assessment, range of motion, a patient satisfaction score, such as a forgotten knee score, a Western Ontario and McMaster Universities Arthritis Index (WOMAC) score, shoulder assessment, hip assessment, etc.). After the patient has opted in, the systems and methods described herein may retrieve stored information from a surgical procedure and relate the stored information to outcome information. The determined relationship (including, for example the stored information and the outcome information) may be used to train a model using machine learning. The model may then be used to evaluate a subsequent surgical procedure to determine whether a recommendation or alert may be issued.

FIG. 1 illustrates a robotic surgery and feedback system 100 in accordance with some embodiments. The system 100 includes a robotic surgical device 102, which may include a computing device 104 (e.g., a processor and memory for performing instructions). The system 100 includes a database 110. The robotic surgical device 102 may be used to perform a portion of a surgical procedure on a patient 108 (e.g., a partial or total knee arthroplasty, a hip arthroplasty, a shoulder arthroplasty, etc.). The robotic surgical device 102 (e.g., via the computing device 104) may store or send data, such as information about an action taken by the robotic surgical device 102 during the portion of the surgical procedure. The data may be sent to the database 110, which may be in communication with a server 112 or user device 114. The system may include a display device 106, which may be used to issue an alert, display information about a recommendation, or receive a request for additional information from a surgeon.

The system 100 may be used to generate or collect data pre-operatively or intra-operatively regarding aspects of a surgical procedure, such as actions taken by the robotic surgical device 102, input from a surgeon, patient anatomy information, or the like. The data may be saved, such as in the database 110, which may be accessed via a server 112 or a user device 114. In an example, the system 100 may generate a code that may be given to a patient after a procedure, such as in a physical copy or electronically sent (e.g., to the user device 114) with the code. The patient may log in to a landing page or portal (e.g., a website), set up an account for the procedure or for the user, and enter the code. The code may be used to access the data from the database 110, where log files of data collected during a procedure may be stored, such as in an anonymized way. Once accessed using the code, the system 100 may retrieve the data for the procedure or the patient. For example, the data may be migrated to the server 112 which may be separate from the database 110 or other server storing the anonymized data. Patient information (e.g., outcome data) may be correlated, combined, or otherwise tied to the procedure or patient data retrieved via the code. The code discussed here is simply one, of potentially many, mechanisms for anonymizing the pre-operative, intra-operative, and post-operative data from the patient information. In this or a similar manner, the system may create a database of deformities, corrective interventions, and outcomes that are correlated, but which are not specifically traceable back to an individual patient without the code or some other identifying information held in a different database. In another example, instead of or in addition to using a code, a machine-readable identifier (e.g., a barcode, a QR code, etc.) may be used. In yet another example, a biometric identification may be used (e.g., fingerprint). Further references to the code throughout this disclosure may include one or more of these identification techniques.

In an example, the patient may be presented one or more questions (e.g., a survey), or asked to supply additional information (e.g., a link to other information, such as a physical or occupational therapy report). In an example, the patient may report outcome information periodically. Any information provided by the patient, after the patient opts in to the system 100 by supplying the code may be stored for processing.

After data is collected, a sub set of patient outcomes that are notable (e.g., good, bad, positive, negative, etc.) may be identified. Using the notable patient outcomes, reasons for the outcomes may be determined from the data generated or captured by the surgical robotic device 102. In an example, the system 100 may be used pre-operatively or intra-operatively to recommend a change in procedure, confirm a step of a procedure, or issue an alert regarding a portion of a procedure. The change, confirmation, or alert may be generated or determined based on the reasons for the outcomes.

In an example, data generated or collected by the surgical robotic device 102 may include data relative to ordinary use of the surgical robotic device 102, data collected on robot use during a procedure, data on use of aspects of the system 100 such as, time spent by a user on a user interface, number of clicks or key presses on a user interface, an adjustment or change to a plan (e.g., pre-operative plan), differences between an original plan and a final plan, duration of use of the surgical robotic device 102, software stability or bugs, or the like. The data collected may be linked using a clinical mechanism to determine whether outcomes are improved. In an example, the data collected may be surgeon specific.

Pre-operative data may include medical imaging of a target procedure site, statistical representations of bones involved in the procedure, virtual models generated of the target procedure site (e.g., a three-dimensional model of a knee joint (distal femur and proximal tibia)), planned implant position and orientation on the virtual models, and planned resections or similar operations to be performed, among other things. Intra-operative data may include soft tissue tension measurements of a joint, intra-operative adjustments to pre-operative plan (implant position/orientation and resections), actual resection parameters (e.g., position and orientation of resections on distal femur) and final implant location (in reference to known landmarks and/or pre-operative plan). Finally, post-operative data may include objective data obtained from follow up medical imaging or other mechanisms to assess implant performance or procedural success, but may also focus on subjective patient impressions and physical performance (e.g., range of motion and strength).

During a procedure, such as in the operating room, a data analytic program may be run (e.g., on the surgical robotic device 102), for example in the background of a knee application. The program may run a simulation in real time to provide insight to the user (e.g., by providing a recommendation, confirmation, or alert). The insight may be based on statistical analysis of historical data and intra-operative decisions or actions taken by the surgeon or using the surgical robotic device 102. In an example, at any step of a given procedure, a recommendation, confirmation, or alert to the surgeon may be updated based on latest actions. This may result in better patient outcome. The data generated or stored by the surgical robotic device 102 during the procedure may be stored (e.g., on the database 110) and used in future procedures.

Figure 2:
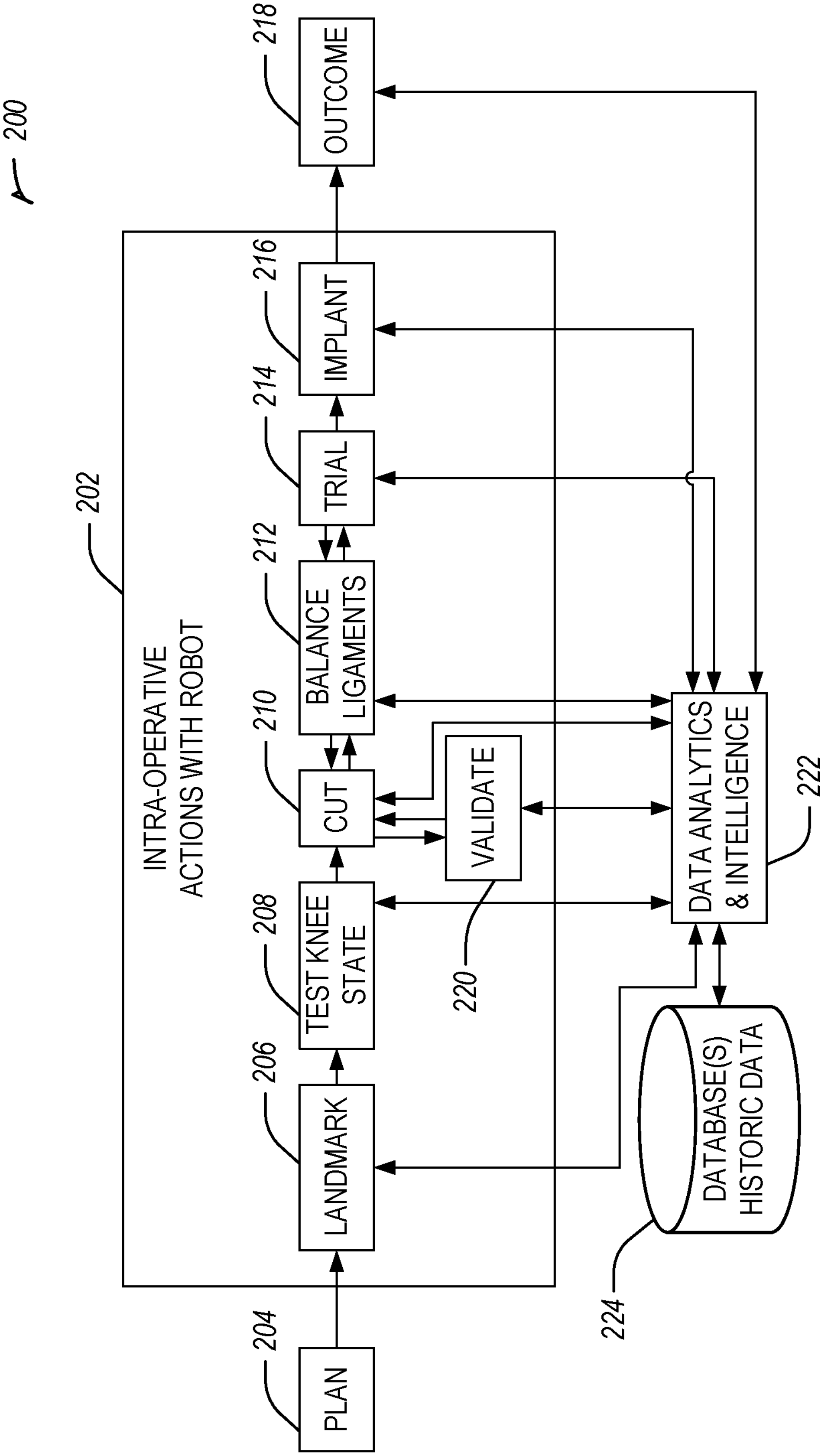
FIG. 2 illustrates a data flow diagram for providing feedback using a robotic surgical device in accordance with some embodiments.

FIG. 2 illustrates a data flow diagram 200 for providing feedback using a robotic surgical device in accordance with some embodiments. In an example, a plan is created or selected at 204, which may be implemented in whole or in part by a robotic surgical device. The robotic surgical device may perform or record intra-operative actions, including landmarking 206, testing a state of anatomy (e.g., a knee or shoulder) 208, performing a cut 210 (which may be validated at 220), balancing soft tissue (e.g., a ligament of the knee) 212, inserting a trial 214, or inserting an implant 216, which may result in an outcome 218. These operations 206-220 may be sent to a data analytics and intelligence engine 222 for determining one or more correlations, one or more causations, or other analytical information from actions taken by or recorded by the robotic surgical device compared to outcomes 218. In an example, the data analytics and intelligence engine 222 may store information in a database 224 or retrieve historical data from the database 224, such as when determining the one or more correlations, the one or more causations, or the other analytical information. In an example, the operations 206-220 may be sent to directly to the database 224, stored in memory of the robotic surgical device, or stored on a portable memory device.

After some amount of historical data is stored (e.g., at the database 224), the data analytics and intelligence engine 222 may send a recommendation (e.g., when requested) or an alert (e.g., when the plan 204 is incomplete or may result in a negative outcome) at any operation 204-220. For example, the historical data (stored in database 224) may be used to compare actions taken (e.g., intra-operative actions with the robot 202) to outcomes 218. The comparison may be performed by a user or via machine learning techniques. The robotic surgical device or other system running in the data flow diagram 200 may provide real-time feedback to a surgeon. For example, a surgeon may develop a plan 204 for a particular cut 210, but a slight misalignment may be made. The surgeon may decide to keep that cut 210, and then the plan 204 may be changed. For example, the historical database 224 may be accessed by the data analytics and intelligence engine 222 to determine successful outcomes 218 in similar circumstances (e.g., output what changes to the plan 204 may be made based on the misaligned cut).

In certain examples, the system may evaluate information being collected in the current procedure against historical data correlated to positive outcomes. For example, at operation 206 the surgeon uses the robotic system to collect a set of landmarks from the actual anatomy that allows for correlation of the pre-operative plan with the specific patient anatomy. While the pre-operative plan was developed from medical images of the specific patient's anatomy, medical imaging is not perfect. Accordingly, the system may determine how well the landmarks collected intra-operatively align with the pre-operative plan. Additionally, machine learning algorithms may evaluate not only how the collected landmarks align with the pre-operative plan in comparison to historically good procedures, but also evaluate how the landmarks themselves compare to previous procedures. For example, the system may determine that certain landmarks exhibit a particular spatial relationship that historically has required a certain modification to a resection or implant position to obtain a positive patient outcome. In such situations, the system may alert the surgeon to the recommended modification based on a correlation the surgeon alone would not have been likely or even capable of detecting.

The data analytics and intelligence engine 222 may develop a recommendation or an alert based on historical data saved in the database 224, after tying the historical data to an outcome 218. In an example, a recommendation or an alert may be determined by extrapolating or interpolating information from the historical data or the outcome 218. For example, the data analytics and intelligence engine 222 may run a simulation or apply a machine learning technique to generate additional data, such as by using the historical data or the outcome 218 as training data for the simulation or the machine learning technique. For example, in the abnormal landmark location example, the system may utilize a linear regression technique to extrapolate an appropriate adjustment to the pre-operative plan based on historical data from procedures with a positive outcome.

In an example, a log file for a procedure may be saved (e.g., in the database 224). The log file may include information saved by a robotic surgical device, and may be added to when outcome 218 information becomes known. Information saved may include such as time spent on the procedure, actions taken by the robotic surgical device, the plan 204, adjustments, etc. The outcome 218 information may include post-operative information such as patient satisfaction, mobility, etc.

A system for providing a recommendation or alert based on the diagram 200 may include a validation feature. For example, to validate at 220 may include using a validation tool, such as to measure the cut 210 to determine an angle of the cut 210. Validation information may be used by the data analytics and intelligence engine 222 to provide an update to the plan 204 (e.g., based on the historical data and outcomes stored in the database 224). The validation tool may include an iAssist device manufactured by Zimmer Biomet of Warsaw, Indiana. The recommendation or alert may include an update to a three-dimensional plan, tracking, navigation, or a remaining procedure. Information related to the recommendation or alert may be provided, such as a on a user interface to the surgeon. The recommendation or alert may be personalized to a particular surgeon, such as based on surgeon preferences, surgeon specific historical data or outcomes, or the like. In an example, the surgeon may request a recommendation at any point during a procedure. The recommendation or alert may be personalized to the patient, for example when previous data about the patient is already stored in the database 224.

Figure 3A:
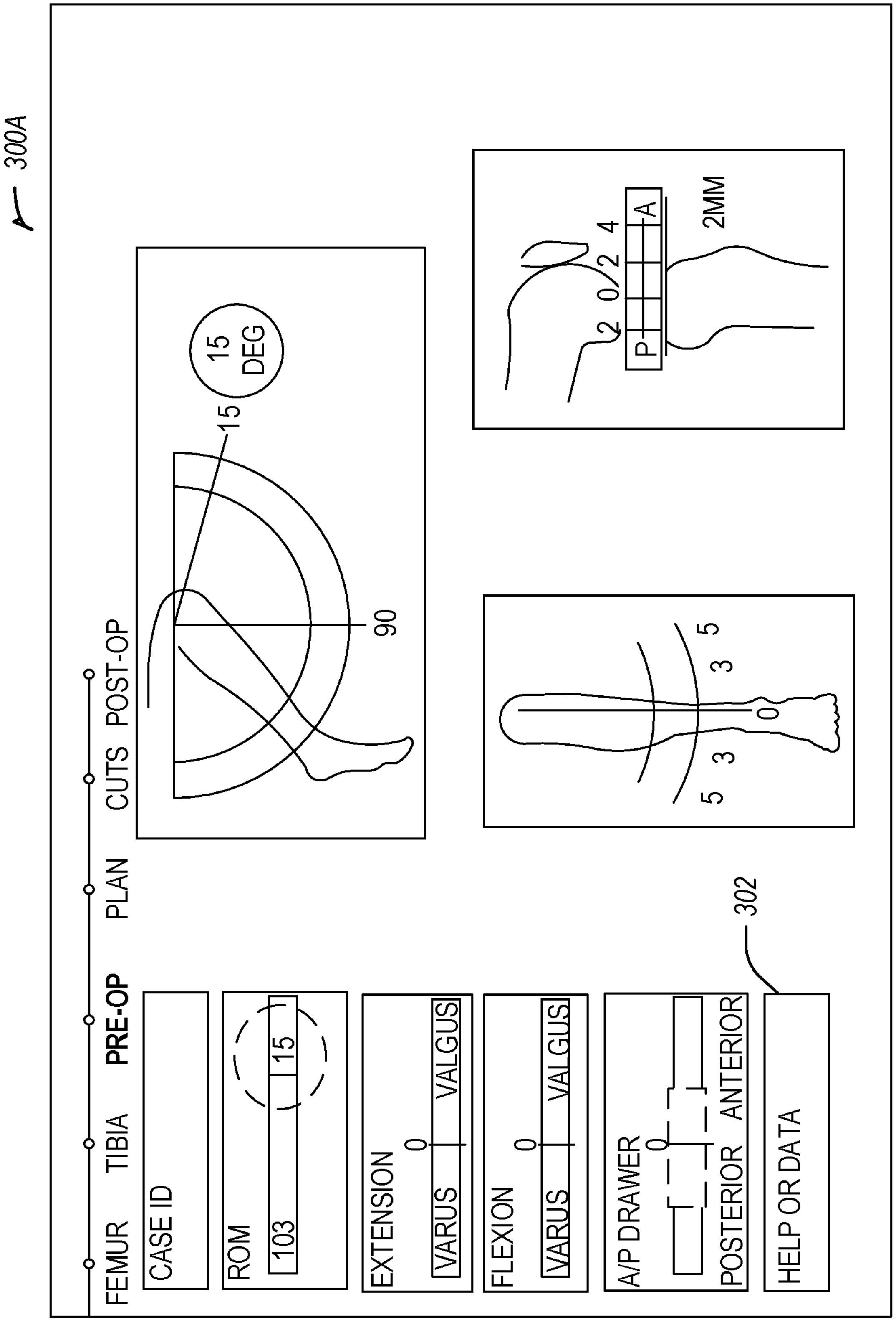
FIGS. 3A-3C illustrate user interfaces for providing feedback to a surgeon in accordance with some embodiments.
Figure 3B:
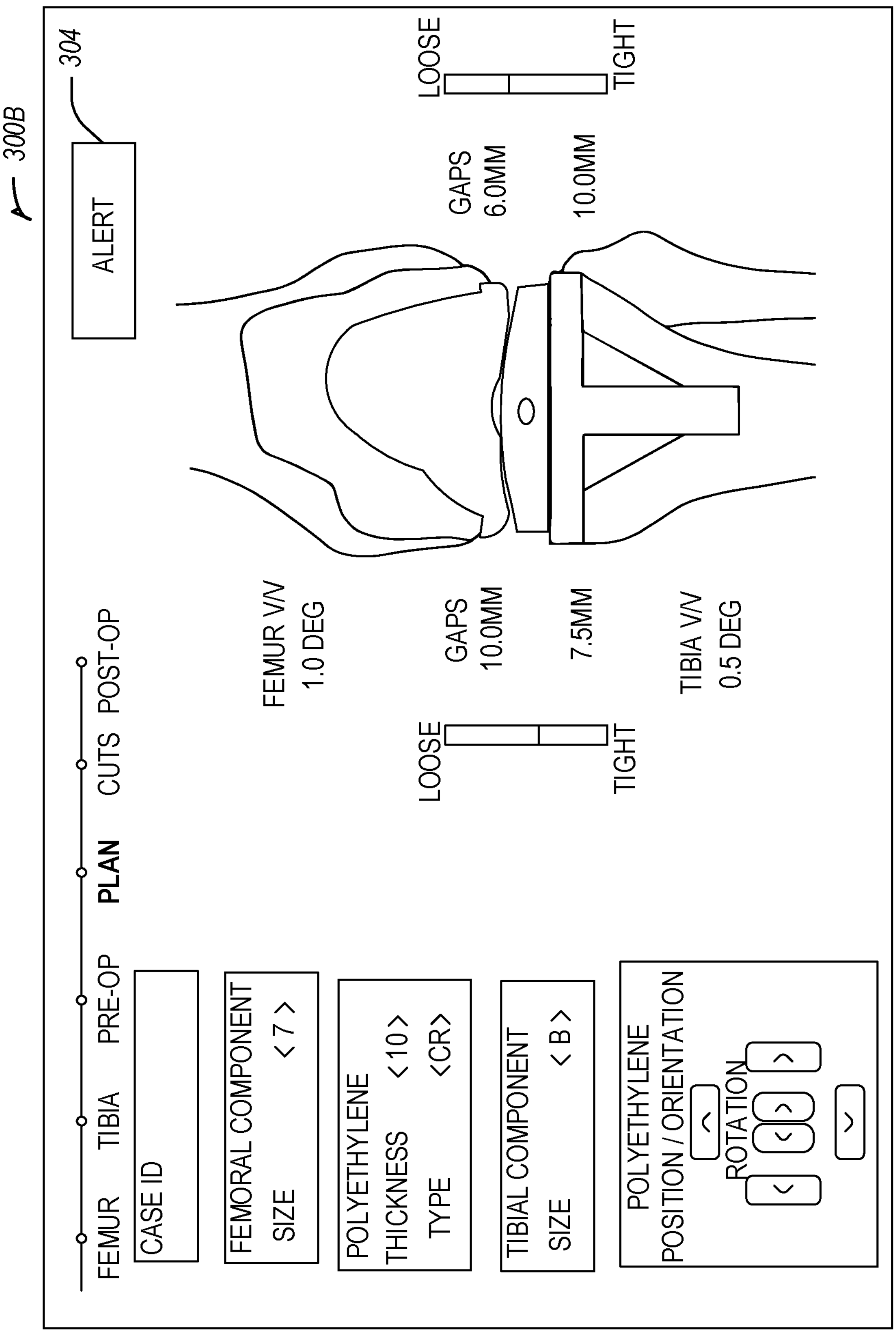
Figure 3C:
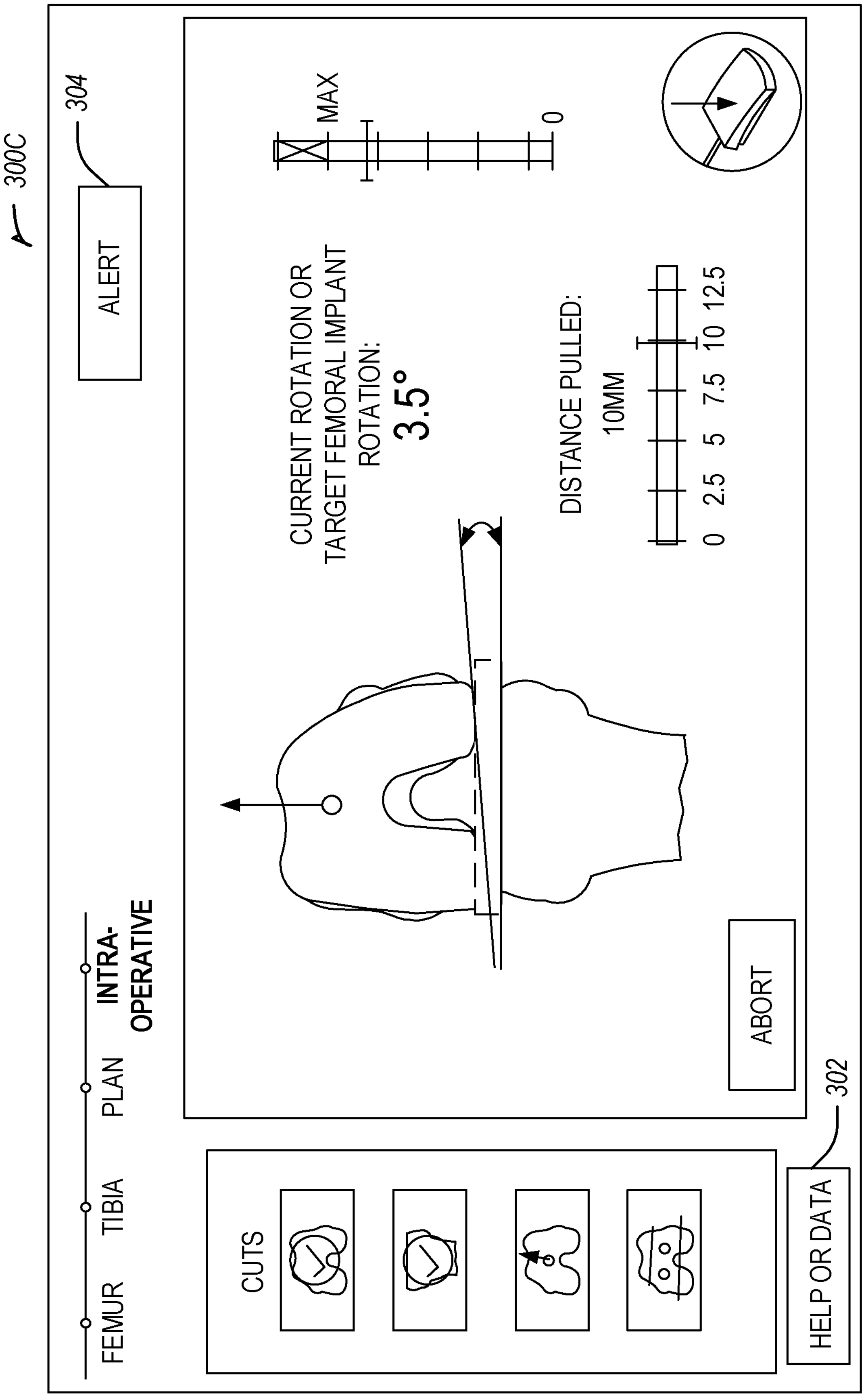

FIGS. 3A-3C illustrate user interfaces 300A-300C for providing feedback to a surgeon in accordance with some embodiments. In an example, one or more of the user interfaces 300A-300C may include a recommendation request interactive component 302. In an example, the user interfaces 300A-300C may include an alert component 304. In another example, the recommendation request interactive component 302 and the alert component 304 may be combined in one component.

The recommendation request interactive component 302 may be selected by a user, such as a surgeon, to receive confirmation of a preoperative or intraoperative plan or a recommendation of a change to the plan. A recommendation system (e.g., as described herein throughout) may be used to present a recommendation, confirmation of no change to a plan, etc., based on actions taken during a surgical procedure.

In an example, the alert component 304 may be used to alert a user (e.g., a surgeon) to a potential change, potential issue, or recommended change to a surgical procedure. The alert component 304 may flash, change color, textually identify an alert, or otherwise alert the user. Additional techniques to alert a user may be used, such as via haptic feedback, audible feedback, a change in surgical lighting, etc.

Figure 4:
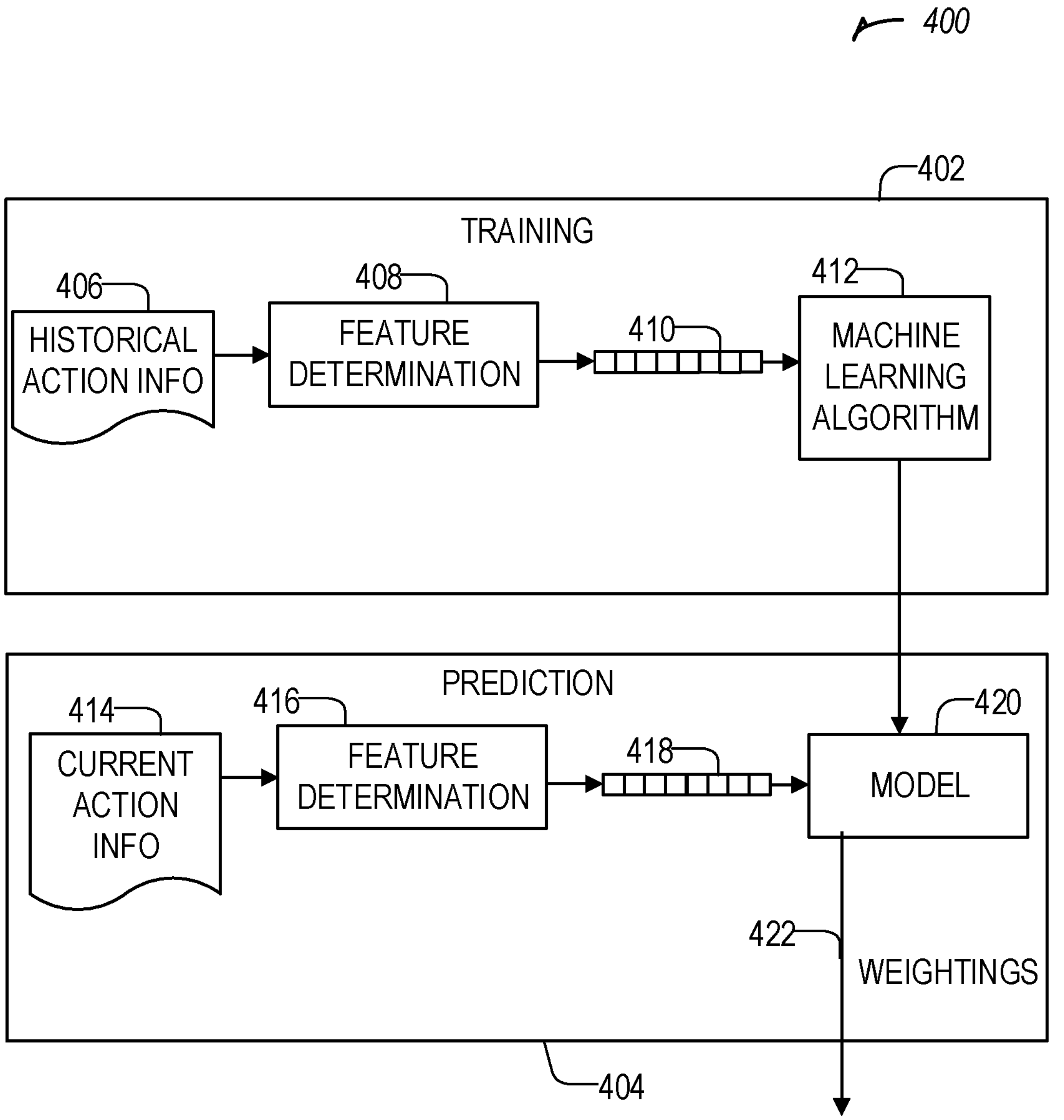
FIG. 4 illustrates a machine learning engine for determining feedback in accordance with some embodiments.

FIG. 4 illustrates a machine learning engine for determining feedback in accordance with some embodiments. A system may calculate one or more weightings for criteria based upon one or more machine learning algorithms. FIG. 4 shows an example machine learning engine 400 according to some examples of the present disclosure. Machine learning engine 400 may be part of the system 100 of FIG. 1, for example implemented using the database 110, the server 112, etc., or the machine learning system 608 of FIG. 6, described below.

Machine learning engine 400 utilizes a training engine 402 and a prediction engine 404. Training engine 402 inputs historical transaction information 406 for historical actions of stored or generated at a robotic surgical device, for example, into feature determination engine 408. The historical action information 406 may be labeled with an indication, such as a degree of success of an outcome of a surgical procedure, which may include pain information, patient feedback, implant success, ambulatory information, or the like. In some examples, an outcome may be subjectively assigned to historical data, but in other examples, one or more labelling criteria may be utilized that may focus on objective outcome metrics (e.g., pain rating, survey score, a patient satisfaction score, such as a forgotten knee score, a WOMAC score, shoulder assessment, hip assessment, or the like).

Feature determination engine 408 determines one or more features 410 from this historical information 406. Stated generally, features 410 are a set of the information input and is information determined to be predictive of a particular outcome. Example features are given above. In some examples, the features 410 may be all the historical activity data, but in other examples, the features 410 may be a subset of the historical activity data. The machine learning algorithm 412 produces a model 420 based upon the features 410 and the labels.

In the prediction engine 404, current action information 414 (e.g., a surgical plan, an action to be taken or a last action taken, such as by a robotic surgical device, or the like) may be input to the feature determination engine 416. Feature determination engine 416 may determine the same set of features or a different set of features from the current information 414 as feature determination engine 408 determined from historical information 406. In some examples, feature determination engine 416 and 408 are the same engine. Feature determination engine 416 produces feature vector 418, which is input into the model 420 to generate one or more criteria weightings 422. The training engine 402 may operate in an offline manner to train the model 420. The prediction engine 404, however, may be designed to operate in an online manner. It should be noted that the model 420 may be periodically updated via additional training or user feedback (e.g., an update to a technique or procedure).

The machine learning algorithm 412 may be selected from among many different potential supervised or unsupervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models. Examples of unsupervised learning algorithms include expectation-maximization algorithms, vector quantization, and information bottleneck method. Unsupervised models may not have a training engine 402. In an example embodiment, a regression model is used and the model 420 is a vector of coefficients corresponding to a learned importance for each of the features in the vector of features 410, 418.

Figure 5A:
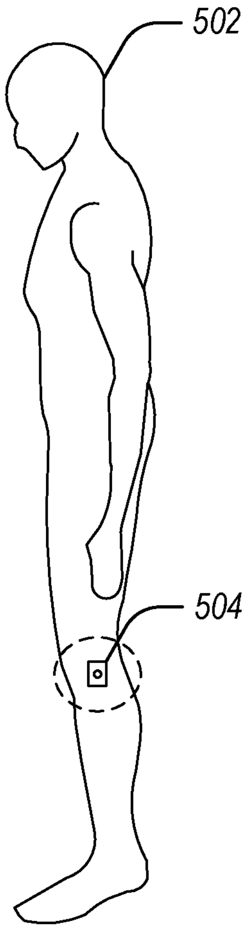
FIGS. 5A-5B illustrate sensor configurations for generating patient outcome information in accordance with some embodiments.
Figure 5B:
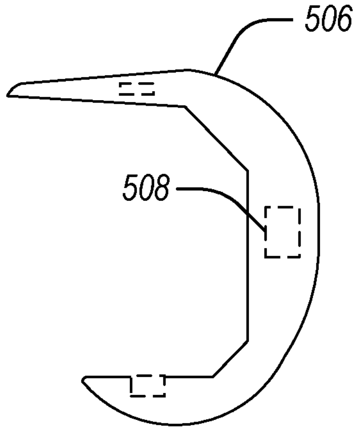

FIGS. 5A-5B illustrate sensor configurations for generating objective patient outcome information in accordance with some embodiments. A sensor may be included in an implantable orthopedic device. The implant may act as a host for the sensor or be the sensor itself. FIG. 5A illustrates an example sensor 504 placements in a knee of a patient 502 in accordance with some examples. The sensor 504 may be placed at various locations on an implant or on a bone. The placement of sensor 504 may vary according to the type of implant, the properties of the bone, or the type of sensor. The sensor 504 may be used to measure or track patient movement, range of motion, pain, fit, a patient satisfaction score, such as a forgotten knee score, a WOMAC score, or the like. The information measured or tracked by the sensor 504 may be saved at a component of the sensor 504 or may be transmitted wirelessly (e.g., using near field communication, RFID, other wireless protocols, such as Bluetooth or Wi-Fi, or the like), such as to a computer or wireless device (e.g., a mobile phone, tablet, wearable device, or the like). In another example, the sensor may be located within a shoulder of a patient (e.g., within an implant).

FIG. 5B depicts various placements on an implant 506 for a sensor 508. The example of FIG. 5B may include an implanted sensor 508 (e.g., a first sensor, a post-operative sensor) associated with a knee joint of the patient. The sensors depicted in FIG. 5B are merely illustrative and other sensors in other locations may be used in examples according to this disclosure.

In an example, a wearable sensor device may be used in addition to or instead of the sensor 504 or 508. In an example, a wearable sensor device may be an off-the-shelf consumer wearable device such as, for example, Fitbit, Jawbone, Apple Watch, or other consumer wearable electronic devices, or sensor device may be a custom sensor that is configured to be worn by a patient to collect pre-operative data or post-operative data. Implanted sensors may be employed to collect pre-operative or post-operative data. In some cases, the sensor may be attached to the patient on, proximate or near the site where an orthopedic surgery may be performed. The sensor may be attached via a garment or strap, however it may also be attached to the patient, for example, via a temporary adhesive.

In some examples, knee sensor technology may include a sensor or sensors to monitor steps, forces, friction, temperature, or the like. Sensors may provide useful data from positions throughout the body. In other examples, shoulder sensor technology may include a sensor or sensors to monitor movement, such as rotation of the shoulder, forces, friction, temperature, or the like.

The example sensors 504 or 508 may include one or more of an accelerometer, a temperature sensor, a force sensor, a resistance sensor, a tachometer, a healing indicator, a pH measure sensor, a tension or compression sensor, callous formation sensing tape, a strain sensor (e.g., strain gauge), a gyroscope or the like. The example sensors 504 or 508 may include active sensors and inactive sensors.

Sensor data may be collected data constantly, or periodically. The collected data may be transmitted, such as routinely, occasionally, or in response to an activation. Activation of a sensor may be based on patient permission, such as post-operation permission when a sensor is included in an implant without pre-operation patient permission to activate. In some examples, access to a sensor in an implant may be an encrypted permission and may rely on an activation code. The data from the sensor may be used to compare a pre-operative plan or an intra-operatively changed plan, to final implant parameters.

Figure 6:
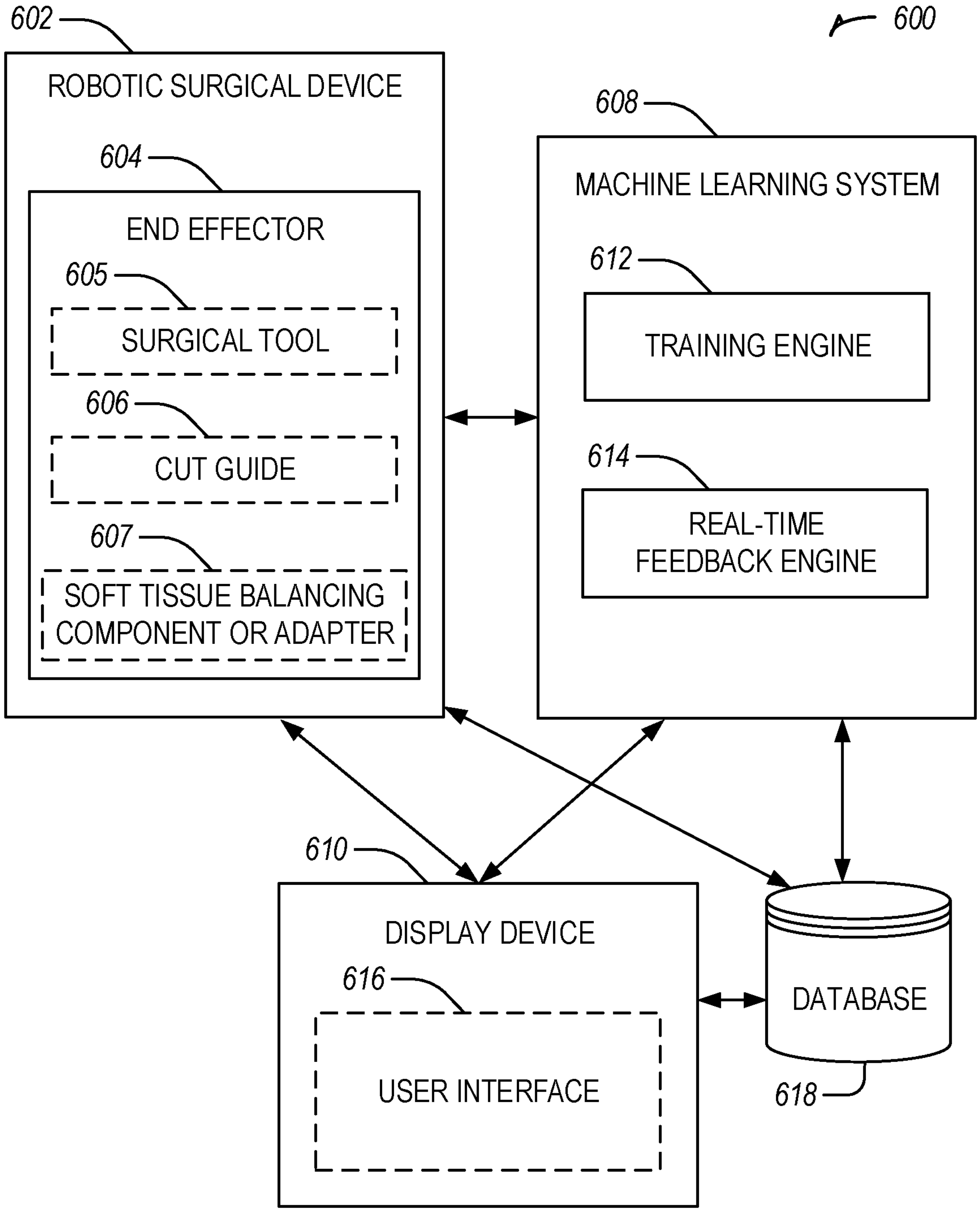
FIG. 6 illustrates a system for pre-operative or intra-operative surgical procedure feedback in accordance with some embodiments.

FIG. 6 illustrates a system 600 for pre-operative or intra-operative surgical procedure feedback in accordance with some embodiments. The system 600 includes a robotic surgical device 602, which may include an end effector 604, such as to attach or manipulate a surgical tool 605, a cut guide 606, a soft tissue balancing component or adapter 607, or the like. The robotic surgical device 602 may output data to a machine learning system 608, a display device 610, or a database 618. In an example, the machine learning system 608 may output information to the display device 610 or a database 618. The display device may retrieve information stored in the database 618. The display device 610 may be used to display a user interface 616. In an example, the machine learning system 608 includes a training engine 612 and a real-time feedback engine 614.

The robotic surgical device 602 may be used to perform a portion of a surgical procedure on a patient. A processor may be coupled to memory (e.g., on the robotic surgical device 602 or the machine learning system 608). The processor may be used to record an action taken by the robotic surgical device 602, such as during the portion of the surgical procedure. The processor may query a database to retrieve information about related prior surgical procedures. In an example, the information may include at least one result or next action taken after the action (e.g., a recommendation or an alert). The processor may determine a recommended change, such as based on the information, to the portion of the surgical procedure or a future aspect of the surgical procedure. The recommended change may be a change as performed by the robotic surgical device 602. The processor may output the recommendation (e.g., to the display device 610). The output may include using the processor or the display device 610 to intraoperatively provide the recommendation to a surgeon operating the robotic surgical device 602. The output may be performed without surgeon input as an alert, or in response to receiving a request for the recommendation, such as on the user interface 616.

In an example, the machine learning system 608 may train using the related prior surgical procedures, including, for example, at least one action taken by the robotic surgical device 602 or at least one corresponding outcome. The at least one corresponding outcome may be based on a patient outcome received from the patient. In an example, the processor may submit a plan to the machine learning system 608 to receive feedback preoperatively or intraoperatively. In an example, the machine learning system 608 may simulate the portion of the surgical procedure to determine a plurality of recommended changes. The machine learning system 608 may select the recommended change from the plurality of recommended changes, such as based on outcome likelihoods of the plurality of recommended changes.

In an example, the recommendation may be surgeon specific, such as based on previous actions taken by the surgeon or based on surgeon preferences. In an example, the robotic surgical device 602 may perform a validation action, and the recommendation or alert may be updated based on the validation action.

In an example, the information about related prior surgical procedures may include patient-specific information about a past procedure performed on the patient (e.g., during a revision surgery, information regarding the previous primary surgery may be considered). In another example, the information about related prior surgical procedures includes demographic-specific information corresponding to the patient. For example, the demographic-specific information may include at least one of patient size (e.g., height, weight, gender, which knee, hip, or shoulder, etc.), surgical procedure type, patient age, or the like.

In an example, the processor may output a post-operative recommendation for the patient, such as including a physical therapy recommendation, based on the information. In an example, the processor may store anonymized data related to the action taken by the robotic surgical device on a first server, receive a code entered by the patient, and pull the anonymous data onto a second server. The processor may tie patient identifying information to the anonymized data on the second server. In an example, the processor may determine a plurality of recommendations, wherein each may have a corresponding action or confidence score. The processor may select the recommendation from the plurality of recommendations based on the confidence score of the recommendation. In another example, the recommendation may include recommending the next action, and wherein the robotic surgical device 602 is further to perform the next action after receiving confirmation from the surgeon.

Figure 7:
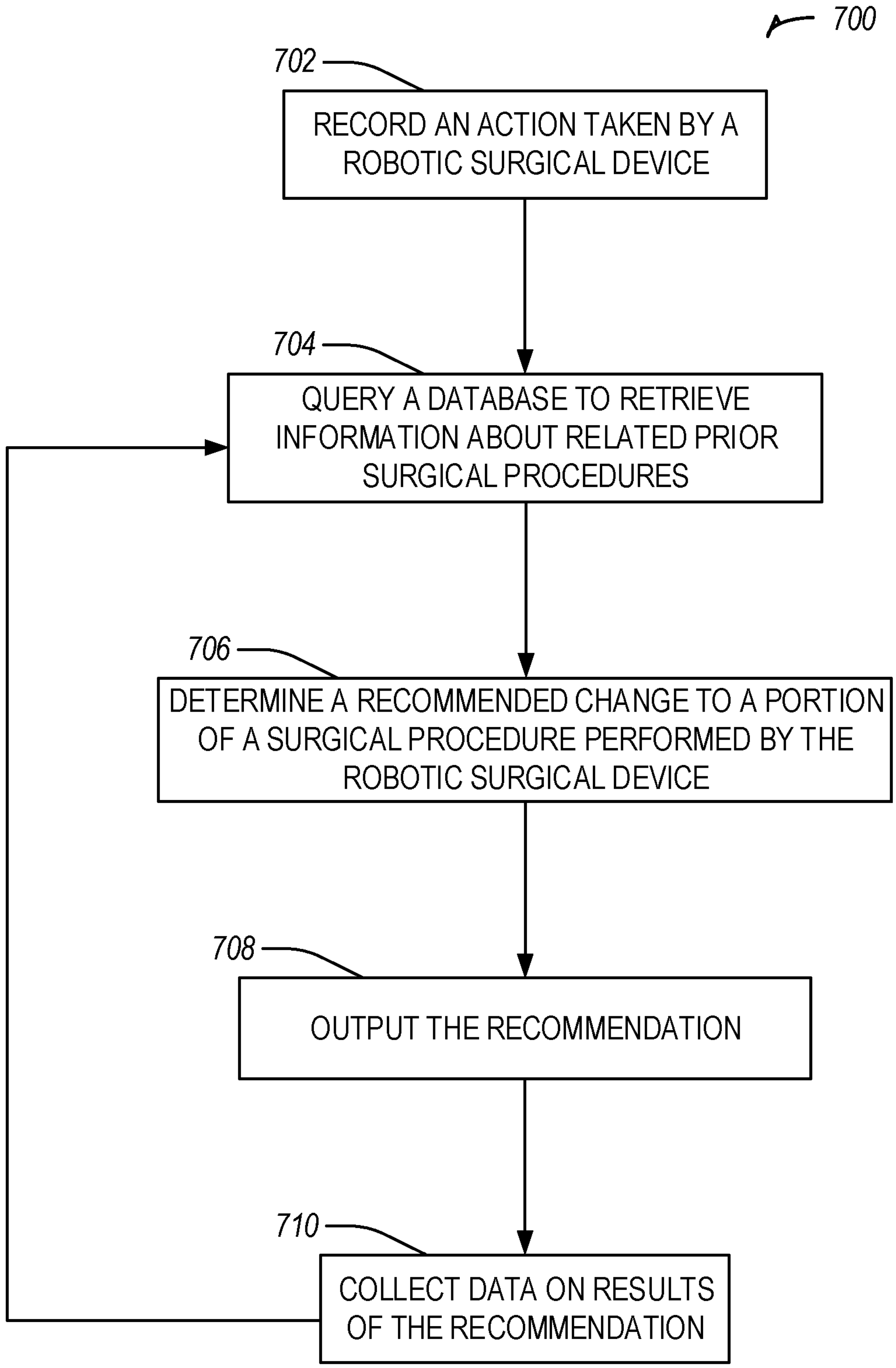
FIG. 7 illustrates a flowchart illustrating a technique for providing intra-operative surgical procedure feedback in accordance with some embodiments.

FIG. 7 illustrates a flowchart illustrating a technique 700 for providing intra-operative surgical procedure feedback in accordance with some embodiments. The technique 700 includes an operation 702 to record an action taken by a robotic surgical device. The technique 700 includes an operation 704 to query a database to retrieve information about related prior surgical procedures. Operation 704 may include retrieving patient-specific information about a past procedure performed on the patient. In an example, the information about related prior surgical procedures includes demographic-specific information corresponding to the patient, such as patient size, surgical procedure type, patient age, or the like. The demographic-specific information may be used to expand the base of related prior surgical procedures to be considered when providing intra-operative surgical procedure feedback beyond just past procedures performed on the specific patient to procedures performed on similarly situated patients.

The technique 700 includes an operation 706 to determine a recommended change to a portion of a surgical procedure performed by the robotic surgical device. The technique 700 includes an operation 708 to output the recommendation. In an example, the recommendation may be a surgeon specific or patient specific recommendation. For example, the recommendation may be based on surgeon preferences. The recommendation may be output without surgeon input as an alert. Operation 708 may include outputting the recommendation in response to receiving a request for the recommendation from the surgeon via a user interface. Operation 708 may include outputting a post-operative recommendation for the patient, such as including a physical therapy recommendation, based on the information. Operation 708 may include recommending the next action. In an example, the robotic surgical device may further perform the next action, such as after receiving confirmation from the surgeon.

The technique 700 includes an operation 710 to collect data on results of the recommendation. Operation 710 may include feeding the collected data back to a database, such as for later retrieval at operation 704 of a latter procedure or portion of a procedure. In an example, the technique 700 may further include an operation to train a machine learning engine using the related prior surgical procedures, for example including at least one action taken by the robotic surgical device or at least one corresponding outcome. In an example, the at least one corresponding outcome is based on a patient outcome received from the patient.

In an example, the technique 700 may further include an operation to submit a plan to a machine learning engine to receive feedback preoperatively. In an example, the technique 700 may further include an operation to simulate the portion of the surgical procedure to determine a plurality of recommended changes. This operation may include selecting the recommended change from the plurality of recommended changes based on outcome likelihoods of the plurality of recommended changes. In an example, the technique 700 may further include an operation to perform a validation action, and updating the recommendation based on the validation action.

In an example, the technique 700 may further include an operation to store anonymized data related to the action taken by the robotic surgical device on a first server, receive a code entered by the patient, and pull the anonymous data onto a second server. This operation may include tying patient identifying information to the anonymized data on the second server. In an example, the technique 700 may further include an operation to determine a plurality of recommendations, for example with each having a corresponding action or confidence score. This operation may include selecting the recommendation from the plurality of recommendations based on the confidence score of the recommendation.

Figure 8:
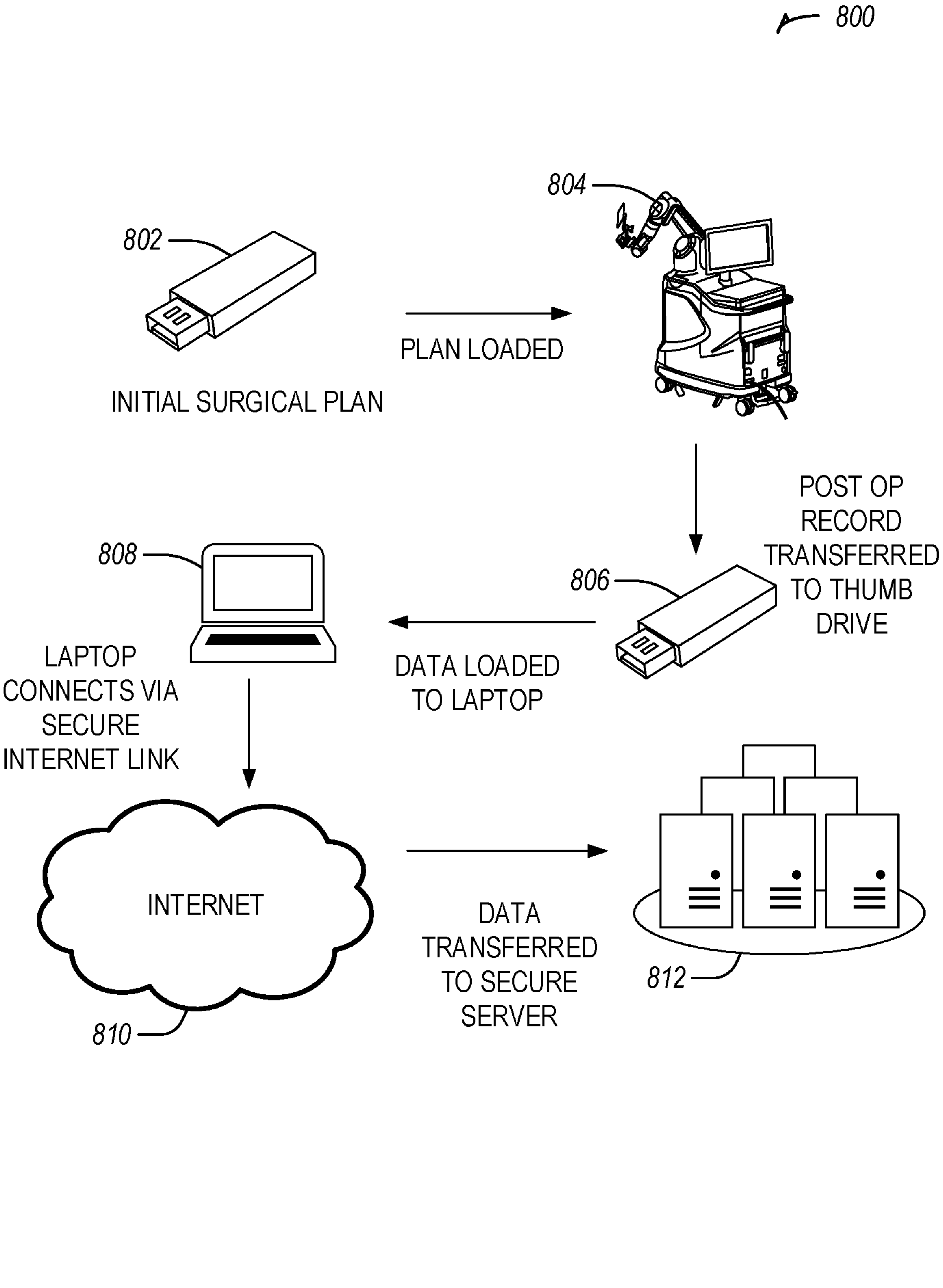
FIG. 8 illustrates a data flow diagram for storing actions of a robotic surgical device in accordance with some embodiments.

FIG. 8 illustrates a data flow diagram 800 for storing actions of a robotic surgical device in accordance with some embodiments. The diagram 800 includes a plurality of operations for loading, saving, and transmitting surgical information among different devices. In an example, a surgical plan may be generated and saved a thumb drive or other storage device at 802. The initial surgical plan may be delivered to a robotic surgical device via the encrypted thumb drive at 804. During a procedure or operation, data may be collected on the robotic surgical device and may be stored to await transfer. After the operation or procedure (e.g., post-op), the data may be transferred from the robotic surgical device to a server via encrypted thumb drive at 806, loaded to an internet connected computer or device at 808, and uploaded via a secure internet or network link to a server at 810. In an example, the data may be stored per procedure, anonymously on the server. The data may be transferred to the secure server at 812. In an example, a coded patient consent field may be stored as part of the record. The coded patient consent field may include a key or code, which may be decrypted in response to receiving a code or key from the patient.

The diagram 800 illustrates actions which may provide feedback to improve patient outcomes and protect patient privacy. For example, the processes described in FIG. 8 may be opt-in based on patient consent. In an example, some information may be recorded via the robotic surgical device 804 and some information submitted later by a patient. These two types of data may be linked to determine whether any actions taken during a procedure affect the outcome. In an example, patient information or feedback may be sought out at intervals. After some data has been collected, the results may be grouped into positive outcomes or negative outcomes, and trends for actions taken during a procedure that lead to those outcomes may be determined. Outcome or action information may be grouped based on one or more attributes of a procedure, such as patient, surgeon, demographic information about the patient, geographic location, duration of procedure, time of day of procedure, day of week of procedure, date of procedure, number of changes to a plan, or the like. Additional information may be used, such as post-operative actions taken by the surgeon or patient (e.g., surgeon follow-up, education, patient physical therapy, adherence to post-op plan, etc.).

After an outcome is associated with actions taken during a procedure, the actions may be evaluated to determine whether one may have caused the outcome. For example, a plurality of positive outcomes or a plurality of negative outcomes may be compared to determine common actions, or actions that are not shared between positive and negative outcomes. For example, soft tissue balancing information may be evaluated such that positive outcomes may be associated with balanced soft tissue. In an example, patients that do not have soft tissue cut during a knee arthroplasty (e.g., ligament releases) may have better outcomes (e.g., for pain, WOMAC score, forgotten knee, etc.) than patients that have soft tissue cut during a knee arthroplasty.

In an example, using the techniques and systems described herein may benefit patients, surgeons, or the medical community. For example, the techniques and systems described herein may allow for expanded clinical research capabilities, and provide case of data entry for clinicians because the robotic surgical device may capture data, using a specified format of data collection for efficient analysis, or the like.

At the end of a surgical procedure, a user operating the robotic surgical device may print or electronically transmit a patient record to give to the patient during or after discharge. The patient record may include general implant information, brand, size, surgeon name, date, or the like. The patient record may include a unique code for accessing the information or opting in to further analysis. The patient may, upon initial home recovery, log on to a user interface that describes the need for clinical information, cadence of outcome forms, description of types of questions, etc., and the patient may then "sign up" for a clinical event.

By signing up, the patient may consent to analysis and access of the patient data to create a link between the anonymous record, and future patient report outcomes, and link the two records. The unique code may trigger population of a second data set, which may include a duplication of only the records that patients have consented to be part of the clinical event. Access may be limited except for clinical research teams, or other groups (e.g., the surgeon) based on patient preference. In an example, the patient may fill out a clinical form at 6 months, 1 year, 2 years, etc.

At given relevant review periods, the data is analyzed for changes in satisfaction levels. Statistical analysis may dictate relevance of clinical findings. When a subset of data reveals higher satisfaction for example, regression analysis may be performed over the second data set to determine whether there is a common data point that explains the improved satisfaction (e.g., a specific action or inaction, such as cutting the soft tissue in a knee arthroplasty, or aligning the implant according to a kinematic vs. mechanical approach). For example, a data set is analyzed, a particular subset of patients have higher satisfaction, regression analysis performed, results in findings, such as patients found to have greater femoral rotation, no medial ligament release, or less tibia rotation. This information may be fed back into a machine learning algorithm, such as described herein.

Figure 9:
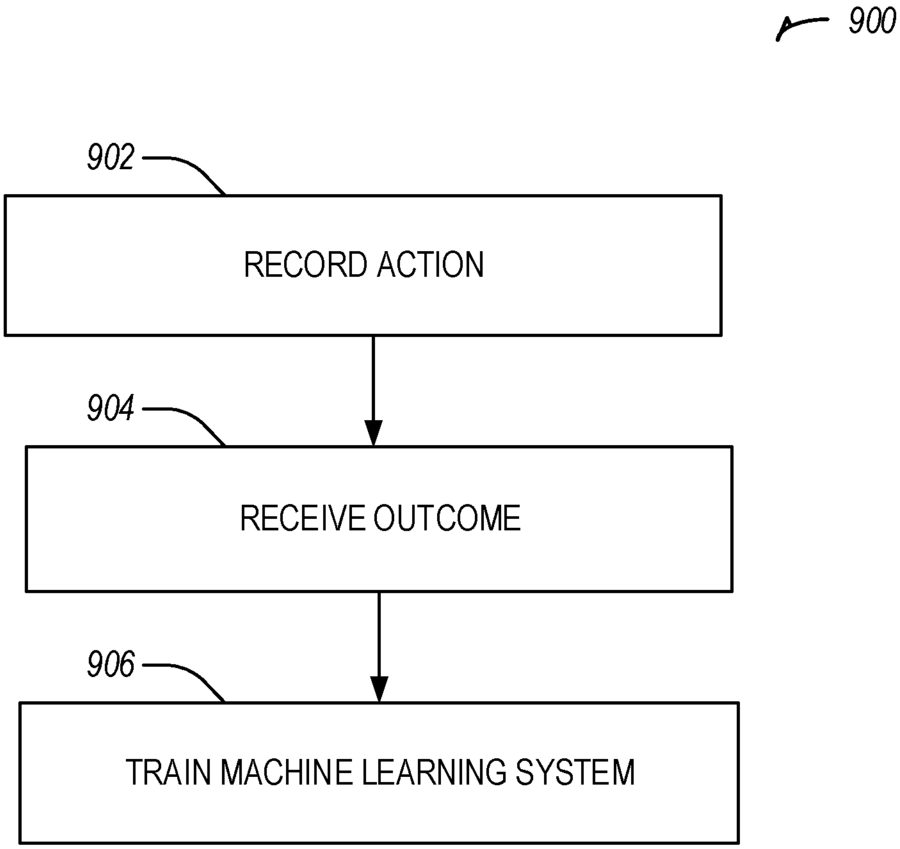
FIG. 9 illustrates a flowchart illustrating a technique for training a machine learning engine to provide pre-operative or intra-operative surgical procedure feedback in accordance with some embodiments.

FIG. 9 illustrates a flowchart illustrating a technique 900 for training a machine learning engine to provide preoperative or intra-operative surgical procedure feedback in accordance with some embodiments.

The technique 900 includes an operation 902 to record an action, such as an action taken by a robotic surgical device during a portion of a surgical procedure. The action may be recorded and saved at the robotic surgical device or output to a storage device. Stored information may include movements of the robotic surgical device, a duration of an action, an input received (e.g., a surgeon input such as a degree of success of a portion of a procedure, a deviation from a plan, etc.), ambient information (e.g., temperature, pressure, lighting details, time of day, day of the week, date, etc.), speed of a procedure, tourniquet time, number of users (e.g., surgeons, nurses, etc.), patient information (e.g., age, gender, weight, height, body mass index (BMI) information, medical history, race, or ethnicity etc., but in an example, not name of the patient or any other identifying information), type of procedure or portion of procedure, anatomical information (e.g., which knee is operated on, varus or valgus, etc.), or the like.

The technique 900 includes an operation 904 to receive outcome information. For example, the outcome information may include objective data (e.g., from a sensor or measured by a medical professional, such as physical therapy progression, walking tests, etc.) or subjective data (e.g., patient pain, patient degree of comfort with the outcome of the procedure, a patient satisfaction score, such as a forgotten knee score, a WOMAC score, shoulder assessment, hip assessment, etc.).

The technique 900 includes an operation 906 to train a machine learning system using the recorded action and related saved information and the outcome information. For example, the machine learning system may be trained to correlate actions taken with outcomes. As described above with respect to FIG. 4, various machine learning techniques may be used to apply weights to inputs, based on training data, to allow for the technique 900 to provide a real-time recommendation or alert when a change or information is identified as potentially relevant to an aspect of a procedure.

Figure 10:
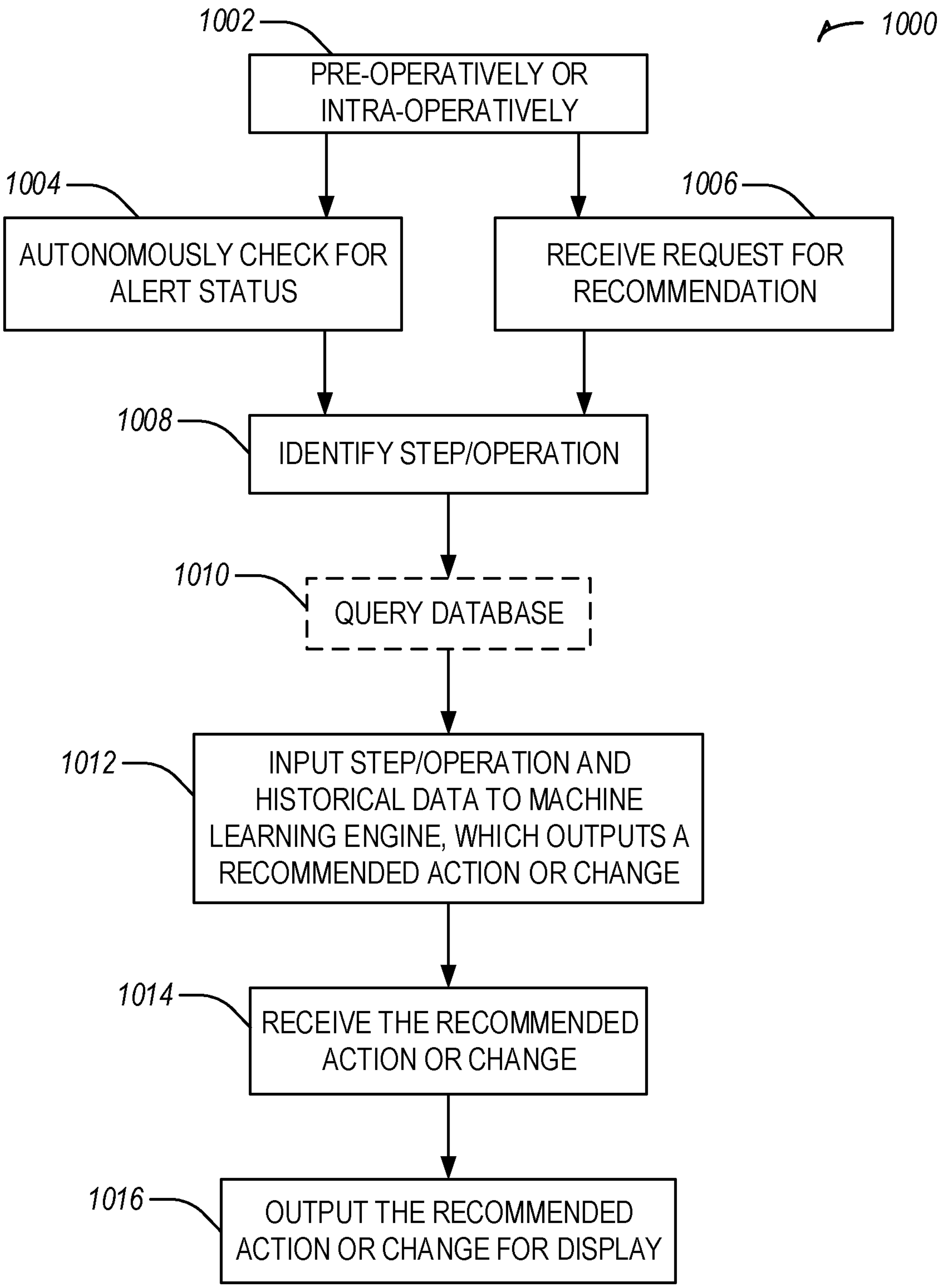
FIG. 10 illustrates a flowchart illustrating a technique for providing pre-operative or intra-operative surgical procedure feedback in accordance with some embodiments.

FIG. 10 illustrates a flowchart illustrating a technique 1000 for providing pre-operative or intra-operative surgical procedure feedback in accordance with some embodiments. The technique 1000 includes an operation 1002 to identify, receive an indication, or select a pre-operative or an intra-operative mode. The technique 1000 may progress to operation 1004 or 1006 or both to proceed.

Operation 1004 includes autonomously checking for an alert status and Operation 1006 includes receiving a request for a recommendation. These two modes may be performed independently or together. For example, the technique 1000 may include checking in real time for an alert status (as described below) and outputting an alert when a particular status occurs. In another example, the technique 1000 may provide a recommendation for an evaluation or change at the request of a user (e.g., surgeon). In yet another example, the technique 1000 includes checking for an alert status and receiving a request for a recommendation, providing the recommendation while continuing to monitor for a change in alert status. The operations to determine whether an alert is to be issued or to determine a recommendation may include operations 1008-1014 described below.

The technique 1000 includes an operation 1008 to identify a step or operation of a portion of a surgical procedure. The technique 1000 includes an optional operation 1010 to query a database. The technique 1000 includes an operation 1012 to input the step or operation and historical data to a machine learning engine, and receive from the machine learning engine a recommended action or change to use as an alert. The technique 1000 includes an operation 1014 to output the recommended action or the alert for display.

Figure 11:
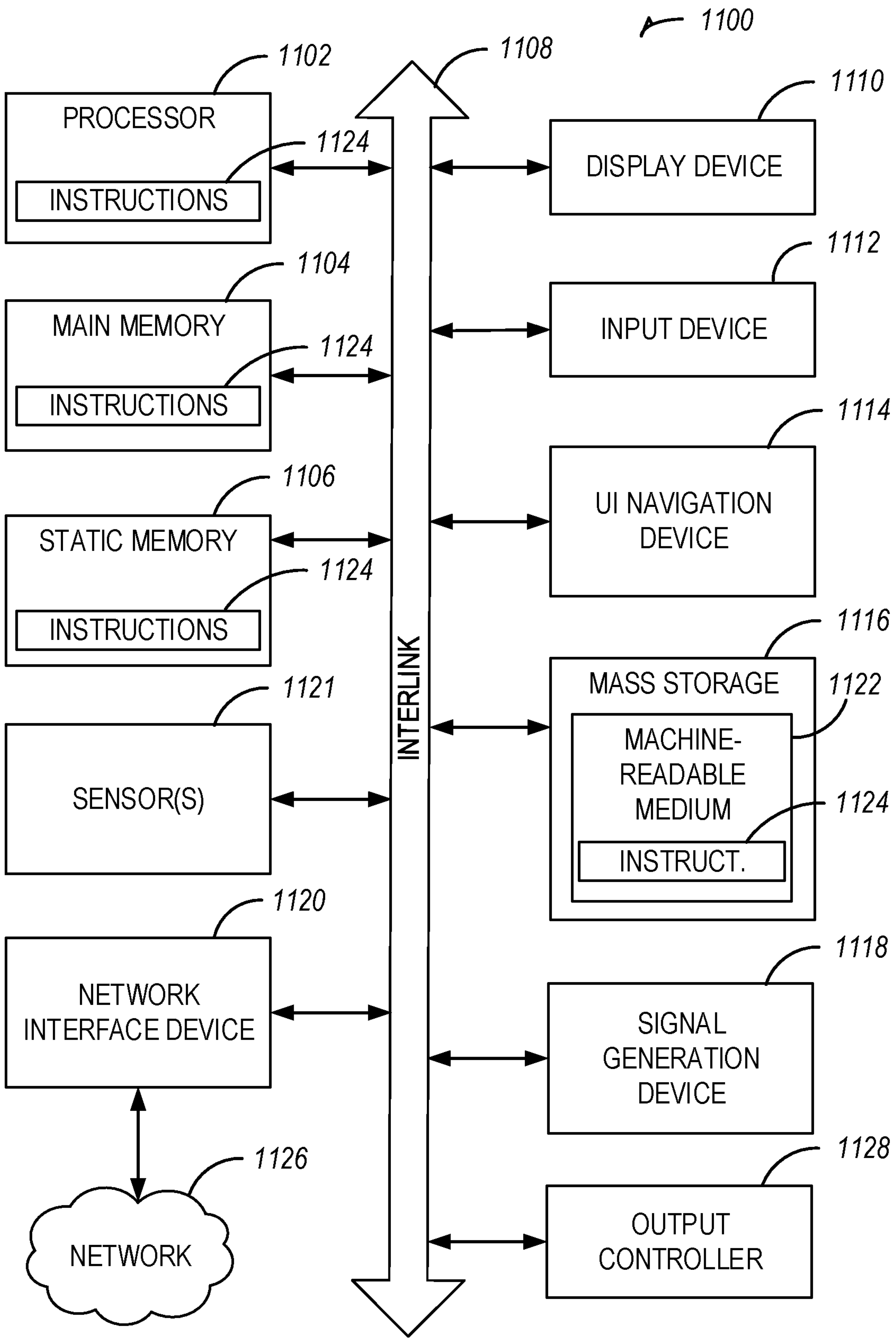
FIG. 11 illustrates a block diagram of an example machine upon which any one or more of the techniques discussed herein may perform in accordance with some embodiments.

FIG. 11 illustrates a block diagram of an example machine 1100 upon which any one or more of the techniques discussed herein may perform in accordance with some embodiments. In alternative embodiments, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110, an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor. The machine 1100 may include an output controller 1128, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine readable medium 1122 is illustrated as a single medium, the term "machine readable medium" may include a single medium or multiple media (e.g., a centralized or distributed database, and/or associated caches and servers) configured to store the one or more instructions 1124. The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a system comprising: a robotic surgical device to perform a portion of a surgical procedure on a patient; a processor and memory including instructions, which when executed by the processor, cause the processor to: record an action taken by the robotic surgical device during the portion of the surgical procedure; query a database to retrieve information about related prior surgical procedures, the information including at least one result or next action taken after the action; determine a recommendation, based on the information, to the portion of the surgical procedure performed by the robotic surgical device; output the recommendation by intra-operatively providing the recommendation to a surgeon operating the robotic surgical device.

In Example 2, the subject matter of Example 1 includes, wherein the system further comprises a machine learning engine and wherein the instructions further cause the processor to: train the machine learning engine using the related prior surgical procedures, including at least one action taken by the robotic surgical device and at least one corresponding outcome.

In Example 3, the subject matter of Example 2 includes, wherein the at least one corresponding outcome is based on a patient outcome received from the patient.

In Example 4, the subject matter of Examples 1-3 includes, wherein the instructions further cause the processor to submit a plan to a machine learning engine to receive feedback preoperatively.

In Example 5, the subject matter of Examples 1-4 includes, wherein the recommendation is a surgeon specific recommendation.

In Example 6, the subject matter of Example 5 includes, wherein the surgeon specific recommendation is based on surgeon preferences.

In Example 7, the subject matter of Examples 1-6 includes, wherein the instructions further cause the processor to simulate the portion of the surgical procedure to determine a plurality of recommended changes, and select the recommended change from the plurality of recommended changes based on outcome likelihoods of the plurality of recommended changes.

In Example 8, the subject matter of Examples 1-7 includes, wherein the robotic surgical device is further to perform a validation action, and wherein the instructions further cause the processor to update the recommendation based on the validation action.

In Example 9, the subject matter of Examples 1-8 includes, wherein to output the recommendation, the instructions cause the processor to output the recommendation without surgeon input as an alert.

In Example 10, the subject matter of Examples 1-9 includes, wherein to output the recommendation, the instructions cause the processor to output the recommendation in response to receiving a request for the recommendation from the surgeon via a user interface.

In Example 11, the subject matter of Examples 1-10 includes, wherein the information about related prior surgical procedures includes patient-specific information about a past procedure performed on the patient.

In Example 12, the subject matter of Examples 1-11 includes, wherein the information about related prior surgical procedures includes demographic-specific information corresponding to the demographics of the patient, the demographic-specific information including at least one of patient size, surgical procedure type, or patient age.

In Example 13, the subject matter of Examples 1-12 includes, wherein the instructions further cause the processor to output a post-operative recommendation for the patient, including a physical therapy recommendation, based on the information.

In Example 14, the subject matter of Examples 1-13 includes, wherein the instructions further cause the processor to: store anonymized data related to the action taken by the robotic surgical device on a first server; receive a code entered by the patient; pull the anonymous data onto a second server; and tie patient identifying information to the anonymized data on the second server.

In Example 15, the subject matter of Examples 1-14 includes, wherein the instructions further cause the processor to determine a plurality of recommendations, each having a corresponding action and confidence score, and select the recommendation from the plurality of recommendations based on the confidence score of the recommendation.

In Example 16, the subject matter of Examples 1-15 includes, wherein the recommendation includes recommending the next action, and wherein the robotic surgical device is further to perform the next action after receiving confirmation from the surgeon.

Example 17 is a method comprising: performing, with a robotic surgical device, a portion of a surgical procedure on a patient; recording, using a processor, an action taken by the robotic surgical device during the portion of the surgical procedure; querying a database to retrieve information about related prior surgical procedures, the information including at least one result or next action taken after the action; determining a recommendation, based on the information, to the portion of the surgical procedure performed by the robotic surgical device; outputting the recommendation by intra-operatively displaying the recommendation to a surgeon operating the robotic surgical device on a display device.

In Example 18, the subject matter of Example 17 includes, training a machine learning engine using the related prior surgical procedures, including at least one action taken by the robotic surgical device and at least one corresponding outcome.

In Example 19, the subject matter of Example 18 includes, wherein the at least one corresponding outcome is based on a patient outcome received from the patient.

In Example 20, the subject matter of Examples 17-19 includes, submitting a plan to a machine learning engine to receive feedback preoperatively.

In Example 21, the subject matter of Examples 17-20 includes, wherein the recommendation is a surgeon specific recommendation.

In Example 22, the subject matter of Example 21 includes, wherein the surgeon specific recommendation is based on surgeon preferences.

In Example 23, the subject matter of Examples 17-22 includes, simulating the portion of the surgical procedure to determine a plurality of recommended changes, and selecting the recommended change from the plurality of recommended changes based on outcome likelihoods of the plurality of recommended changes.

In Example 24, the subject matter of Examples 17-23 includes, performing a validation action, and updating the recommendation based on the validation action.

In Example 25, the subject matter of Examples 17-24 includes, wherein outputting the recommendation includes outputting the recommendation without surgeon input as an alert.

In Example 26, the subject matter of Examples 17-25 includes, wherein outputting the recommendation includes outputting the recommendation in response to receiving a request for the recommendation from the surgeon via a user interface.

In Example 27, the subject matter of Examples 17-26 includes, wherein the information about related prior surgical procedures includes patient-specific information about a past procedure performed on the patient.

In Example 28, the subject matter of Examples 17-27 includes, wherein the information about related prior surgical procedures includes demographic-specific information corresponding to the patient, the demographic-specific information including at least one of patient size, surgical procedure type, or patient age.

In Example 29, the subject matter of Examples 17-28 includes, outputting a post-operative recommendation for the patient, including a physical therapy recommendation, based on the information.

In Example 30, the subject matter of Examples 17-29 includes, storing anonymized data related to the action taken by the robotic surgical device on a first server; receiving a code entered by the patient; pulling the anonymous data onto a second server; and tying patient identifying information to the anonymized data on the second server.

In Example 31, the subject matter of Examples 17-30 includes, determining a plurality of recommendations, each having a corresponding action and confidence score, and selecting the recommendation from the plurality of recommendations based on the confidence score of the recommendation.

In Example 32, the subject matter of Examples 17-31 includes, wherein outputting the recommendation includes recommending the next action, and wherein the robotic surgical device is further to perform the next action after receiving confirmation from the surgeon.

Example 33 is at least one machine-readable medium including instructions for operation of a computing system, which when executed by a machine, cause the machine to perform operations of any of the methods of Examples 1-32.

Example 34 is an apparatus comprising means for performing any of the methods of Examples 1-32.

Example 35 is a device to implement of any of Examples 1-32.

Example 36 is a method to implement of any of Examples 1-32.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system comprising:

a robotic surgical device to automatically perform a portion of a surgical procedure on a patient and capture robotic surgical operation data associated with the portion of the surgical procedure;

a prediction engine and a feature determination engine, the feature determination engine to generate a set of robotic surgical procedure weights based on a correlation of each of a plurality of pre-operative deformities with each of a plurality of successful intra-operative interventions taken by the robotic surgical device, the plurality of successful intra-operative interventions determined by identifying, from among a plurality of intra-operative interventions, a subset of interventions that are associated with favorable post-operative surgical outcome data, the favorable post-operative surgical outcome data identified based on a longitudinal recovery trajectory generated from recovery data generated over a plurality of post-operative time points by a patient-associated sensor, the longitudinal recovery trajectory including objective recovery measurements that change over time; and a processor and memory including instructions, which when executed by the processor, cause the processor to:

record an action taken by the robotic surgical device during the portion of the surgical procedure;

intra-operatively input the action taken by the robotic surgical device to the prediction engine;

generate, in response to the action taken being input at the prediction engine, a robotic surgical procedure prediction output at the prediction engine based on an application of the set of robotic surgical procedure weights to the action taken by the robotic surgical device, the robotic surgical procedure prediction output including at least one result or next action taken after the action;

determine a robotic surgical procedure recommendation intra-operatively, based on the robotic surgical procedure prediction output, to the portion of the surgical procedure performed by the robotic surgical device; and output the robotic surgical procedure recommendation by intra-operatively providing the robotic surgical procedure recommendation to a surgeon operating the robotic surgical device.

2. The system of claim 1, further including a surgical user interface device to receive a confirmation to execute the robotic surgical procedure recommendation;

the instructions further causing the processor to instruct the robotic surgical device to perform a modified surgical procedure based on the robotic surgical procedure recommendation.

3. The system of claim 2, wherein the surgical user interface device includes a touchscreen display device to:

display a user interface for providing the robotic surgical procedure recommendation to the surgeon; and receive the confirmation to execute the robotic surgical procedure recommendation.

4. The system of claim 1, wherein:

the robotic surgical procedure recommendation is specific to the surgeon operating the robotic surgical device; and the robotic surgical procedure recommendation is based on at least one of a set of surgical preferences associated with the surgeon or a set of previous surgical actions taken by the surgeon.

5. The system of claim 1, the instructions further causing the processor to:

preoperatively submit a surgical plan to the prediction engine;

preoperatively receive a surgical procedure success prediction from the prediction engine; and preoperatively generate a predicted surgical procedure outcome based on the surgical procedure success prediction.

6. The system of claim 1, the instructions further causing the processor to:

simulate the portion of the surgical procedure to determine a plurality of recommended changes; and select the robotic surgical procedure recommendation from the plurality of recommended changes based on predicted outcomes.

7. The system of claim 1, the instructions further causing the processor to:

store anonymized data related to the action taken by the robotic surgical device on a first server;

receive a code entered by the patient;

pull the anonymized data onto a second server; and tie patient identifying information to the anonymized data on the second server.

8. The system of claim 1, the instructions further causing the processor to:

store anonymized data related to the action taken by the robotic surgical device;

receive a patient identifying code entered by the patient; and associate patient identifying information with the anonymized data based on the patient identifying code.

9. A method comprising:

recording an action taken by a robotic surgical device during a portion of a surgical procedure, the robotic surgical device to automatically perform the portion of the surgical procedure on a patient and capture robotic surgical operation data associated with the portion of the surgical procedure;

intra-operatively inputting the action taken by the robotic surgical device to a prediction engine, the prediction engine configured to generate a robotic surgical procedure prediction output based on a set of robotic surgical procedure weights, the set of robotic surgical procedure weights generated at a feature determination engine based on a correlation of each of a plurality of pre-operative deformities with each of a plurality of successful intra-operative interventions taken by the robotic surgical device, the plurality of successful intra-operative interventions determined by identifying, from among a plurality of intra-operative interventions, a subset of interventions that are associated with favorable post-operative surgical outcome data, the favorable post-operative surgical outcome data identified based on a longitudinal recovery trajectory generated from recovery data generated over a plurality of post-operative time points by a patient-associated sensor, the longitudinal recovery trajectory including objective recovery measurements that change over time;

generating, in response to the action taken being input at the prediction engine, a robotic surgical procedure prediction output at the prediction engine based on an application of the set of robotic surgical procedure weights to the action taken by the robotic surgical device, the robotic surgical procedure prediction output including at least one result or next action taken after the action;

determining a robotic surgical procedure recommendation intra-operatively, based on the robotic surgical procedure prediction output, to the portion of the surgical procedure performed by the robotic surgical device; and outputting the robotic surgical procedure recommendation by intra-operatively providing the robotic surgical procedure recommendation to a surgeon operating the robotic surgical device.

10. The method of claim 9, further including:

receiving, at a surgical user interface device, a confirmation to execute the robotic surgical procedure recommendation; and instructing the robotic surgical device to perform a modified surgical procedure based on the robotic surgical procedure recommendation.

11. The method of claim 10, further including:

displaying a user interface on the surgical user interface device for providing the robotic surgical procedure recommendation to the surgeon, the surgical user interface device including a touchscreen display; and receiving the confirmation to execute the robotic surgical procedure recommendation.

12. The method of claim 9, wherein:

the robotic surgical procedure recommendation is specific to the surgeon operating the robotic surgical device; and the robotic surgical procedure recommendation is based on at least one of a set of surgical preferences associated with the surgeon or a set of previous surgical actions taken by the surgeon.

13. The method of claim 9, further including:

preoperatively submitting a surgical plan to the prediction engine;

preoperatively receiving a surgical procedure success prediction from the prediction engine; and preoperatively generating a predicted surgical procedure outcome based on the surgical procedure success prediction.

14. The method of claim 9, further including:
simulating the portion of the surgical procedure to determine a plurality of recommended changes; and
selecting the robotic surgical procedure recommendation from the plurality of recommended changes based on predicted outcomes.

15. The method of claim 9, further including:
storing anonymized data related to the action taken by the robotic surgical device on a first server;
receiving a code entered by the patient;
pulling the anonymized data onto a second server; and
tying patient identifying information to the anonymized data on the second server.

16. The method of claim 9, further including:
storing anonymized data related to the action taken by the robotic surgical device;
receiving a patient identifying code entered by the patient; and
associating patient identifying information with the anonymized data based on the patient identifying code.

17. The method of claim 9, further including generating a post-operative recommendation for the patient based on the robotic surgical procedure prediction output.

18. A non-transitory computer-readable medium storing instructions that, when executed by a processor of a device, cause the device to:
record an action taken by a robotic surgical device during a portion of a surgical procedure, the robotic surgical device to automatically perform the portion of the surgical procedure on a patient and capture robotic surgical operation data associated with the portion of the surgical procedure;
intra-operatively input the action taken by the robotic surgical device to a prediction engine, the prediction engine configured to generate a robotic surgical procedure prediction output based on a set of robotic surgical procedure weights, the set of robotic surgical procedure weights generated at a feature determination engine based on a correlation of each of a plurality of pre-operative deformities with each of a plurality of successful intra-operative interventions taken by the robotic surgical device, the plurality of successful intra-operative interventions determined by identifying, from among a plurality of intra-operative interventions, a subset of interventions that are associated with favorable post-operative surgical outcome data, the favorable post-operative surgical outcome data identified based on a longitudinal recovery trajectory generated from recovery data generated over a plurality of post-operative time points by a patient-associated sensor, the longitudinal recovery trajectory including objective recovery measurements that change over time;
generate, in response to the action taken being input at the prediction engine, a robotic surgical procedure prediction output at the prediction engine based on an application of the set of robotic surgical procedure weights to the action taken by the robotic surgical device, the robotic surgical procedure prediction output including at least one result or next action taken after the action;
determine a robotic surgical procedure recommendation intra-operatively, based on the robotic surgical procedure prediction output, to the portion of the surgical procedure performed by the robotic surgical device; and
output the robotic surgical procedure recommendation by intra-operatively providing the robotic surgical procedure recommendation to a surgeon operating the robotic surgical device.

19. The non-transitory computer-readable medium of claim 18, the instructions further causing the device to:
receive, at a surgical user interface device, a confirmation to execute the robotic surgical procedure recommendation; and
instruct the robotic surgical device to perform a modified surgical procedure based on the robotic surgical procedure recommendation.

20. The non-transitory computer-readable medium of claim 19, the instructions further causing the device to:
display a user interface on the surgical user interface device for providing the robotic surgical procedure recommendation to the surgeon, the surgical user interface device including a touchscreen display; and
receive the confirmation to execute the robotic surgical procedure recommendation.

* * * * *